(12) United States Patent
Paul, Jr. et al.

(10) Patent No.: US 9,398,902 B2
(45) Date of Patent: *Jul. 26, 2016

(54) VESSEL CLOSURE DEVICE

(75) Inventors: Ram H. Paul, Jr., Bloomington, IN (US); Brian L. Bates, Bloomington, IN (US); Cleon Stanley, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 308 days.

This patent is subject to a terminal disclaimer.

(21) Appl. No.: 13/497,708

(22) PCT Filed: Sep. 20, 2010

(86) PCT No.: PCT/US2010/049505
§ 371 (c)(1),
(2), (4) Date: Mar. 22, 2012

(87) PCT Pub. No.: WO2011/037866
PCT Pub. Date: Mar. 31, 2011

(65) Prior Publication Data
US 2012/0179172 A1    Jul. 12, 2012

Related U.S. Application Data

(60) Provisional application No. 61/244,684, filed on Sep. 22, 2009.

(51) Int. Cl.
*A61B 17/128* (2006.01)
*A61B 17/122* (2006.01)
(Continued)

(52) U.S. Cl.
CPC ............. *A61B 17/0057* (2013.01); *A61B 17/29* (2013.01); *A61B 2017/0034* (2013.01); *A61B2017/00473* (2013.01); *A61B 2017/00575* (2013.01); *A61B 2017/146* (2013.01); *A61B 2017/2905* (2013.01); *A61B 2017/2931* (2013.01); *A61B 2017/303* (2013.01)

(58) Field of Classification Search
CPC ................. A61B 17/0057; A61B 2017/00473; A61B 2017/00575; A61B 2017/00676; A61B 2017/00584; A61B 17/29; A61B 17/30; A61B 17/08; A61B 17/083; A61B 2017/00619; A61B 2017/00309; A61B 2017/303; A61B 2017/081
USPC .......... 606/142, 151, 213, 215–216, 219–221
See application file for complete search history.

(56) References Cited

U.S. PATENT DOCUMENTS 4,222,380 A * 9/1980 Terayama ..................... 604/115
4,444,380 A    4/1984 Chambers et al.
(Continued)

FOREIGN PATENT DOCUMENTS

WO    WO 2005/027753 A1    3/2005
WO    WO 2010021969 A1 *  2/2010

OTHER PUBLICATIONS

International Search Report for PCT Application No. PCT/US 2010/049505 mailed Mar. 31, 2011. (3 pgs).

*Primary Examiner* — Julian W Woo
*Assistant Examiner* — Shaun L David
(74) *Attorney, Agent, or Firm* — Brinks Gilson & Lione

(57) ABSTRACT

A device and system for closure of an opening formed in a body vessel includes a bioabsorbable grasping member and locking member. The grasping member includes grasping lingers that are radially collapsible to the closed positions by movement of the locking member over the fingers. A distal portion of the fingers is configured to grasp an outer wall portion of the body vessel surrounding the opening when the fingers are in the open position. Movement of the locking member can cause the fingers to at least substantially close the vessel opening. Structural features on the fingers and/or locking member can inhibit proximal or distal movement of the locking member when in a locking position. A detachable arm can be coupled to the grasping member to facilitate placement of the grasping member. A sheath can fit over the detachable arm and be configured to move the locking member over the fingers.

25 Claims, 20 Drawing Sheets

(51) Int. Cl.
*A61B 17/00* (2006.01)
*A61B 17/29* (2006.01)
*A61B 17/14* (2006.01)
*A61B 17/30* (2006.01)

(56) References Cited

U.S. PATENT DOCUMENTS

| | | | |
|---|---|---|---|
| 4,509,517 A * | 4/1985 | Zibelin | 606/127 |
| 5,100,418 A * | 3/1992 | Yoon et al. | 606/139 |
| 5,300,086 A * | 4/1994 | Gory et al. | 606/200 |
| 5,445,167 A | 8/1995 | Yoon et al. | |
| 5,944,728 A * | 8/1999 | Bates | 606/127 |
| 5,984,950 A * | 11/1999 | Cragg et al. | 606/216 |
| 8,298,244 B2 * | 10/2012 | Garcia et al. | 606/127 |
| 2001/0053923 A1 * | 12/2001 | Sato et al. | 606/215 |
| 2005/0075665 A1 * | 4/2005 | Brenzel et al. | 606/213 |
| 2006/0122647 A1 | 6/2006 | Callaghan et al. | |
| 2008/0243106 A1 * | 10/2008 | Coe et al. | 606/1 |

* cited by examiner

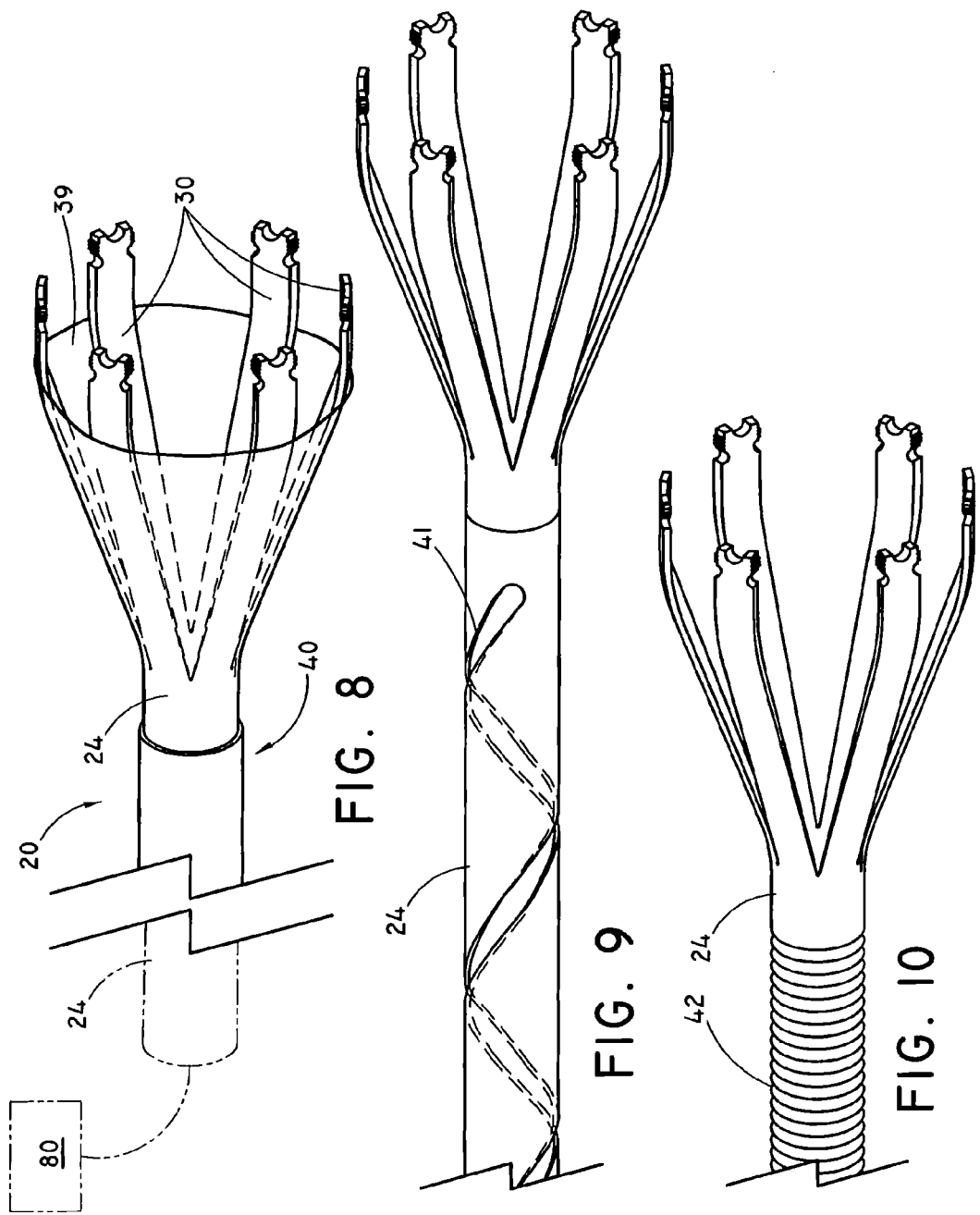

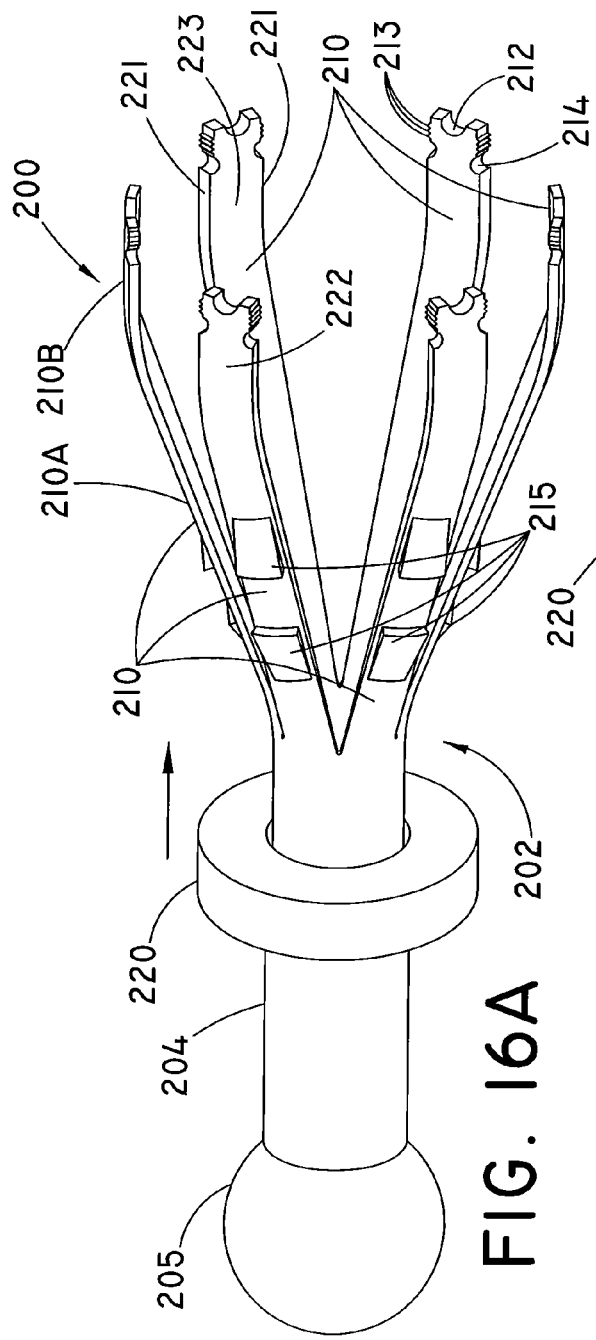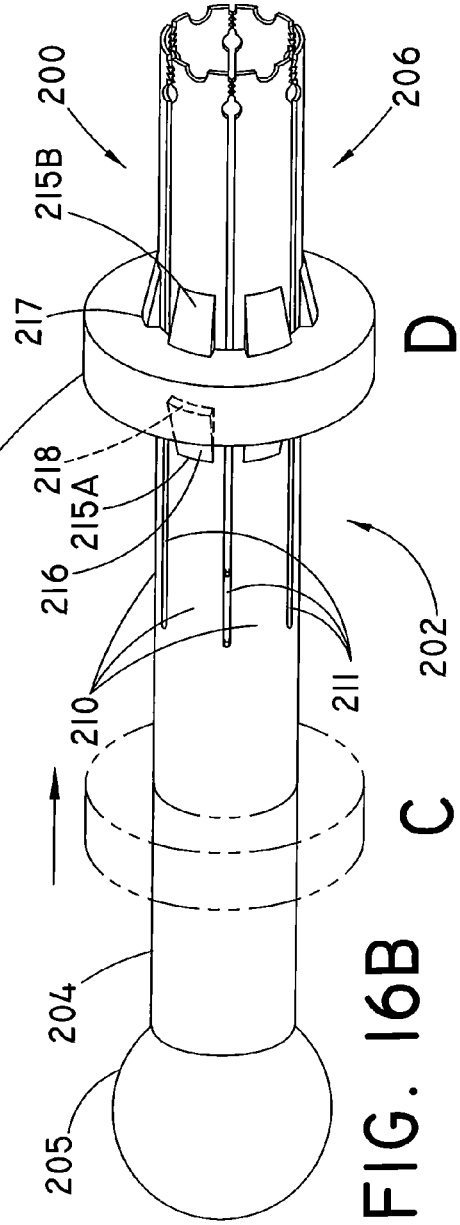
FIG. 16A
FIG. 16B

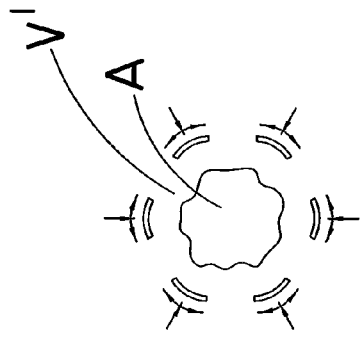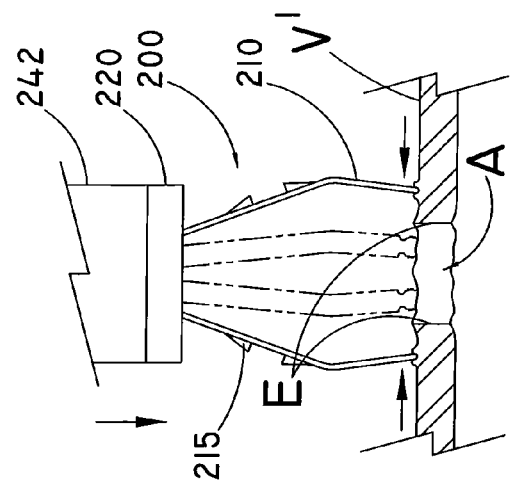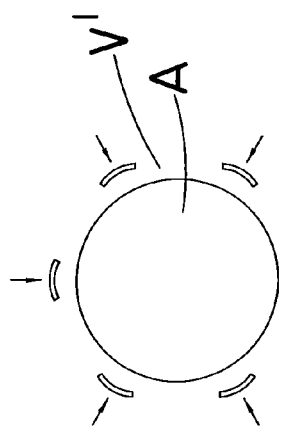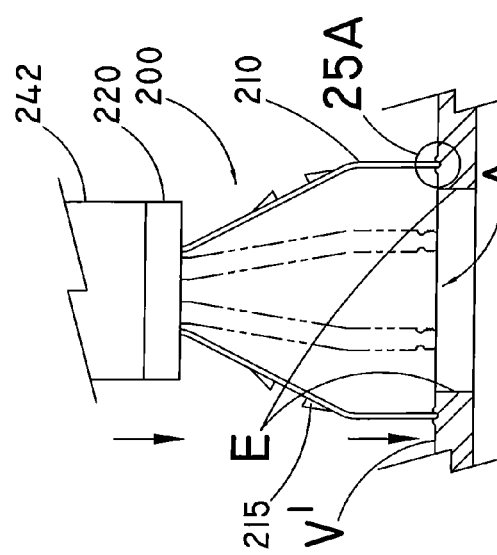

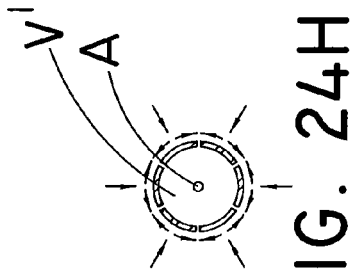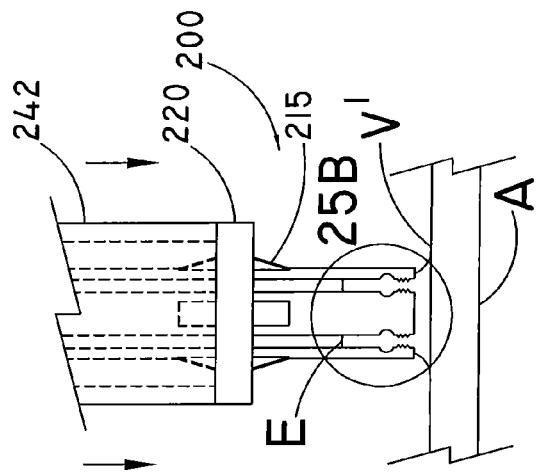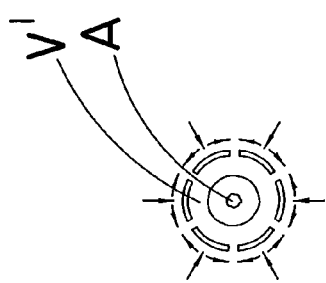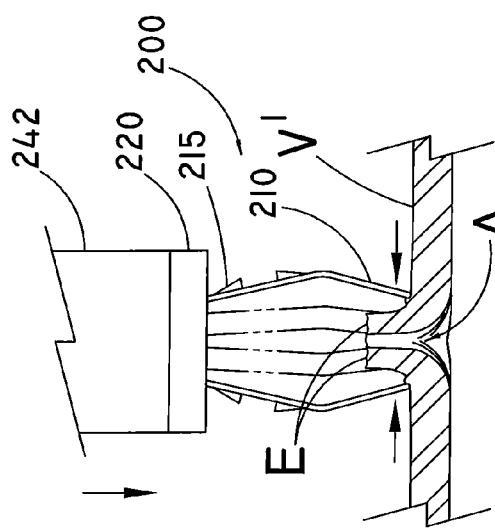

VESSEL CLOSURE DEVICE

This application is a National Stage of International Application PCT/US2010/49505 filed Sep. 20, 2010, which claims the benefit of the filing date under 35 U.S.C. §119(e) of Provisional U.S. patent application Ser. No. 61/244,684, filed Sep. 22, 2009. The entirety of both applications is hereby incorporated by reference.

BACKGROUND

This invention relates to the field of medical apparatuses. More particularly, the invention relates to a device for closure of an access site of a body vessel, such as a blood vessel.

Numerous advances of considerable note have occurred in medical surgical techniques over the last few decades. Among the most significant advances has been the adoption, and now-routine performance, of a variety of minimally invasive procedures. These minimally invasive procedures are distinguishable from conventional open surgical procedures in that access to a body vessel of a patient, such as a blood vessel, is achieved through a relatively small incision through the wall of the vessel. A tubular medical device (or tubular portion of a device) may be inserted or introduced through the incision into the interior space of the vessel for carrying out a medical procedure. The tubular device, or device portion, keeps the incision open while permitting access to the vessel via the interior passageway of the tubular device.

When carrying out such minimally invasive procedures, communication with the lumen of the vessel is typically attained by inserting an access device, such as an introducer sheath, through the opening in the vessel wall. One typical procedure for inserting the introducer sheath is the well-known Seldinger percutaneous entry technique. In the Seldinger technique, a needle is initially inserted into the vessel, and a wire guide is inserted into the vessel through a bore of the needle. The needle is withdrawn, and an introducer assembly is inserted over the wire guide into the vessel opening. Typically, the introducer assembly includes an outer introducer sheath, and an inner dilator having a tapered distal end. The tapered end of the dilator stretches the opening in the vessel in controlled fashion, so that introduction of the larger diameter introducer sheath may then be carried out with a minimum of trauma to the patient.

Following advancement of the introducer sheath into the opening, the dilator is removed, leaving at least the distal portion of the larger diameter introducer sheath in place in the vessel. The introducer sheath is generally provided with a valve at its proximal end for inhibiting leakage of body fluids through the introducer. A catheter may be inserted through the valve and the lumen of the introducer sheath. The catheter is threaded over the wire guide, and the distal end of the catheter is inserted into position in the vessel for carrying out the medical procedure. As a result, the introducer sheath can facilitate insertion of various devices into the vessel while minimizing trauma to the vessel wall and minimizing blood loss during the procedure. Upon completion of the medical procedure, the catheter and introducer sheath are generally removed, leaving a puncture at the vessel access site.

The puncture at the vessel access site is typically closed by suturing, or by manually providing pressure on the site until clotting and/or wound sealing occurs. Suturing is more often utilized for larger punctures, whereas manual pressure is more often utilized in connection with smaller punctures. The manual method, however, can take half an hour or more, and requires the patient to remain substantially immobilized for at least that period of time while pressure is applied by medical personnel to the access site. In addition, it may be necessary for the patient to remain in the hospital for a period of time thereafter for observation. Furthermore, there may be a possibility of clot formation at the puncture site.

Utilizing sutures and/or collagen plugs to close the opening may have procedure variability, which may require additional time to close the vessel. When sutures are utilized to close a larger vessel access site, they typically are of the "purse-string" type. In this type of suture, a single thread is stitched to surround the access site, and then pulled tight (like a purse-string) to close the access site. Performing this suture typically requires a good deal of skill and practice on the part of the physician. It also may be difficult to perform this type of suturing in a key-hole type procedure, or in other types of surgery where there is limited access to the wound site.

It is desired to provide a device for closure of a vessel access site that overcomes the problems of the prior art. It is also desired to provide a bioabsorbable device that need not be removed from the patient following closure of the vessel access site.

SUMMARY OF THE INVENTION

In one example, an implantable grasper for closure of an opening in a body vessel wall is provided. The grasper can include a grasping member and a locking member, which both can be bioabsorbable. The grasping member can have a proximal portion and a distal portion. The proximal portion can include a body and a proximal end. The distal portion can include a plurality of fingers that extend radially from a distal end of the body at a first angle. The fingers are collapsible from the first angle to a second angle. A distal portion of the fingers is configured to grasp an outer wall portion of the body vessel surrounding the opening when the fingers are extended at the first angle. The locking member can be slidably received over a portion of the grasping member. The locking member can be configured to collapse the fingers from the first angle to the second angle to cause the collapsed fingers to at least substantially close the vessel opening. At least one of the fingers of the grasping member and the locking member can be structured and arranged to inhibit the locking member from axial movement in either a proximal direction or a distal direction after the fingers are collapsed. For example, the fingers and/or the locking member can include structural features such as protrusions or recesses. The distal portion of the fingers may have one or more of the following features: one or more first cut-out portions at an axial end of the distal portion; one or more teeth along at least one of the lateral sides of the fingers; and a second cut-out portion along at least one of the lateral sides proximal of the teeth.

In another example, a system for closure of an opening in a body vessel wall of a body is provided. The system can include a bioabsorbable grasping member, a bioabsorbable locking member, and a detachable arm. The grasping member can have a proximal end, a proximal body, and a plurality of collapsible fingers extending radially from a distal end of the proximal body. A distal portion of the fingers can be configured to grasp an outer wall portion of the body vessel that surrounds the opening when the fingers are extended in an open position. The distal portion of the fingers may have one or more of the following features: one or more first cut-out portions at an axial end of the distal portion; one or more teeth along at least one of the lateral sides of the fingers; and a second cut-out portion along at least one of the lateral sides proximal of the teeth. The locking member can be slidably coupled over a portion of the grasping member. The locking member is movable to collapse the fingers from the open position to a closed position to cause the collapsed fingers to at least substantially close the vessel opening. The detachable arm can be removably attached to the grasping member so that the grasping member and the locking member can remain in the body after detachment of the detachable arm from the grasping member. Various configurations of the coupling between the detachable arm and the grasping member are provided, where the advantages of each configuration will become apparent from the description below. The system may further include a sheath that is configured to move the locking member, and an introducer sheath is configured to deliver the system to the vessel opening.

In yet another example, a method for closing an opening at an access site in a body vessel is also provided. The method can include one or more of the following steps: providing one embodiment of a closure device as described below, a stabilizing member engageable with the proximal portion of the grasping member, and a locking sheath slidable over the stabilizing member and at least a portion of the grasping member of the closure device; arranging the grasping member to the open position such that the distal portion of the fingers engage tissue surrounding the opening; and advancing the locking sheath over the stabilizing member and a length of the grasping member, such that the locking sheath engages and advances a closing member of the closure device over a length of the fingers a position surrounding the fingers, thereby collapsing the fingers to the closed position to at least substantially close the vessel opening at the access site in the body vessel. The detachable arm can be detached from the closure device so that the closure device remains within the body.

BRIEF DESCRIPTION OF THE DRAWINGS

FIG. 8 illustrates an alternative embodiment of the closure device of FIG. 1, including an expandable member extending around the fingers of the device;

FIG. 9 illustrates an alternative embodiment of the closure device of FIG. 1, including a spiral slot formed along the tubular body of the grasping member;

FIG. 10 illustrates an alternative embodiment of the closure device of FIG. 1, including a helical member disposed along a length of the tubular body of the grasping member;

FIG. 16A is a side view of a grasper according to an embodiment of the present invention in an open position;

FIG. 16B is a side view of the grasper in FIG. 16A in a closed position;

FIGS. 24A-D are side views of another example of use of the grasper of FIG. 16A;

FIGS. 24E-H are top views corresponding to FIGS. 24A-D, of use of the grasper of FIG. 16A.

DETAILED DESCRIPTION OF THE DRAWINGS AND THE PRESENTLY PREFERRED EMBODIMENTS

Figure 1:
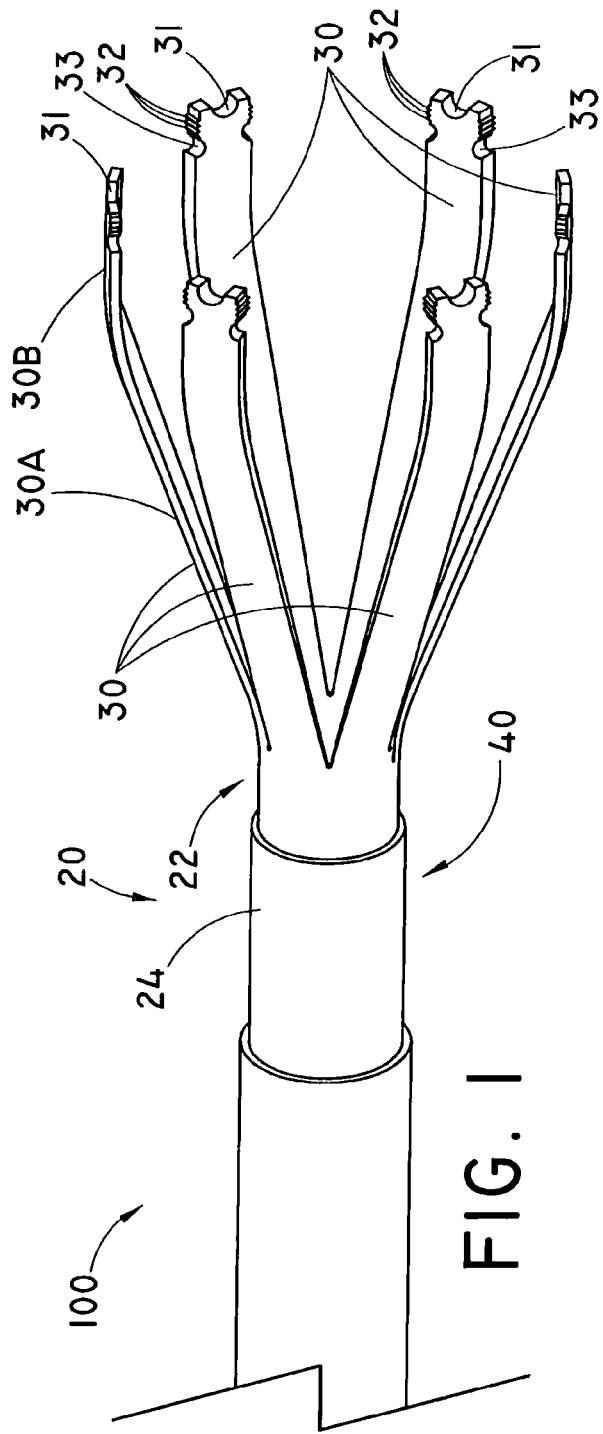
FIG. 1 is a side view of one embodiment of a device for closure of a vessel access site.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the inventive vessel closure device, as well as the axial ends of various component features. The term "proximal" is used in its conventional sense to refer to the end of the device (or component thereof) that is closest to the operator during use of the device. The term "distal" is used in its conventional sense to refer to the end of the device (or component thereof) that is initially inserted into the patient, or that is closest to the patient during use.

FIG. 1 illustrates a side view of one embodiment of a device 20 for closure of a vessel access site. As described herein, use of device 20 allows for rapid and minimally invasive closure of an opening formed through a wall of a body vessel, such as a blood vessel, during a medical procedure that has previously been carried out at the site.

As illustrated in FIG. 1, device 20 includes two main components, namely, a grasping member 22 and a sheath 40 overlying a proximal portion of the grasping member. Also illustrated in FIG. 1 is the distal end of a conventional introducer sheath 100 through which closure device 20 may be introduced into a body passageway for passage to the affected vessel site in conventional fashion.

Figure 2:
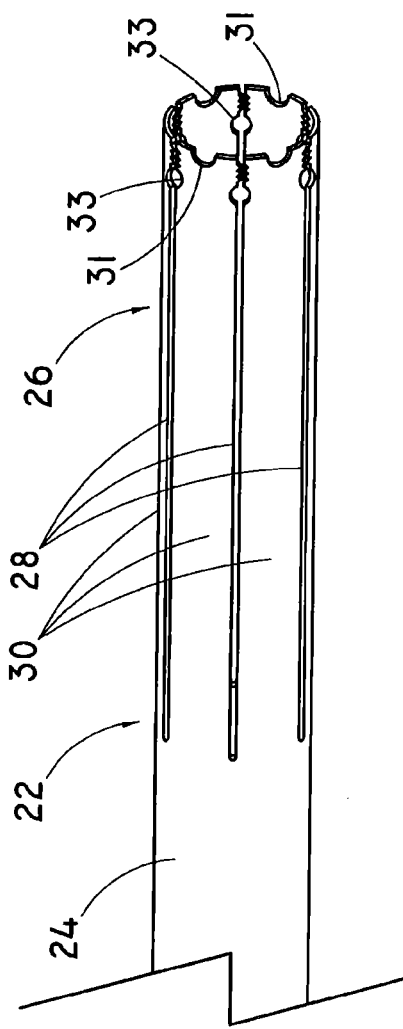
FIG. 2 is a side view of the distal end of the tubular body portion of the device of FIG. 1 prior to shaping the tubular body portion.
Figure 3:
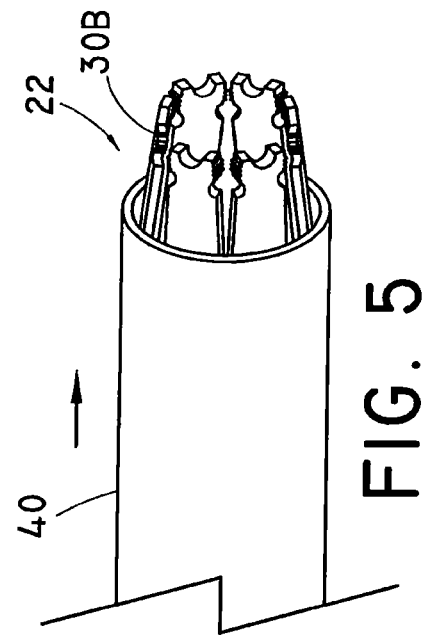
FIG. 3 illustrates partial shaping of the tubular body portion illustrated in FIG. 2.

To provide a better understanding of structure of the grasping member 22, FIGS. 2 and 3 illustrate two stages that may be carried out for forming the grasping member. Preferably, grasping member 22 is formed from a relatively rigid biocompatible tubular structure, such as a metal, metal alloy, or relatively rigid polymeric tube. Non-limiting examples of particularly suitable materials for forming grasping member 22 include a spring metal, such as stainless steels (e.g., 316, 316L or 304); nickel-titanium alloys including shape memory or superelastic types (e.g., nitinol or elastinite); inconel; noble metals including copper, silver, gold, platinum, palladium and iridium; refractory metals including molybdenum, tungsten, tantalum, titanium, rhenium, or niobium; stainless steels alloyed with noble and/or refractory metals; magnesium; amorphous metals; plastically deformable metals (e.g., tantalum); nickel-based alloys (e.g., including platinum, gold and/or tantalum alloys); iron-based alloys (e.g., including platinum, gold and/or tantalum alloys); cobalt-based alloys (e.g., including platinum, gold and/or tantalum alloys); cobalt-chrome alloys (e.g., elgiloy); cobalt-chromium-nickel alloys (e.g., phynox); alloys of cobalt, nickel, chromium and molybdenum (e.g., MP35N or MP20N); cobalt-chromium-vanadium alloys; cobalt-chromium-tungsten alloys; platinum-iridium alloys; platinum-tungsten alloys; magnesium alloys; titanium alloys (e.g., TiC, TiN); tantalum alloys (e.g., TaC, TaN); L605; magnetic ferrite; bioabsorbable materials as described below; or other biocompatible metals and/or alloys thereof.

As shown in FIGS. 2 and 3, grasping member 22 includes a tubular main body portion 24, and a distal portion 26 extending therefrom. Typically, tubular main body portion 24 will have a generally circular cross section, although tubular body members having other geometrical cross sections, such as an elliptical, square, etc., may alternatively be utilized. A series of slits 28 are cut, e.g., by laser cutting, along the length of distal portion 26. Preferably, six slits 28 are cut along the circumference of distal portion 26 as shown. Ultimately, following final shaping of the grasping member as further described herein, slits 28 define six grasping fingers 30. Slits 28 may be formed to have any desired length to enable closure device 20 to perform the functions described herein. Preferably, slits (and therefore fingers 30) will have a length of about 3-15 mm, and more preferably, about 6 mm. Those skilled in the art will appreciate that other numbers and dimensions of slits may be formed, resulting in the formation of other numbers and/or sizes of grasping fingers.

Grasping member 22 will typically have a length such that the proximal end of the grasping member extends in the proximal direction beyond the proximal end of the introducer sheath 100. This arrangement permits easy access to the proximal end of grasping member by the user. Thus, for example, grasping member 22 will typically have a length between about 15 and 120 cm. The exact length of the grasping member is generally not critical, but as stated, such length will typically slightly exceed the length of the introducer sheath in order to provide access at the proximal end as described.

The precise outer diameter of the grasping member is also typically not critical. Preferably, however, such outer diameter will generally be within a range of about 0.75 and 2 mm, such as about 1.2 mm.

Along with the series of slits 28, additional features may also be cut along the length of distal portion 26. When present, these optional features assist in grasping and securing tissue surrounding the vessel access site without piercing the vessel wall. Thus, for example, as shown in the embodiment depicted in FIGS. 3, 3A, and 6, a cut-out portion, such as the generally semicircular groove 31 shown in the figures, may be cut into a generally flat distal tip 34 of each finger. When present, the grooves 31, or similar structure, function in the nature of a "stop" along the generally flat distal tip to limit penetration of the finger 30 into the tissue of the vessel wall during use, by allowing the tissue to fold into the grasping finger without piercing the tissue.

One or more teeth 32 (three are shown in the figures), or similar structure (e.g., teeth in the nature of barbs) may be cut or otherwise formed into the sides of the fingers. When present, teeth 32 assist in grasping the tissue, and preventing the tissue from slipping out when it is caught between the fingers. Any number and shape of teeth or other structure may be provided, so long as the structure is capable of grasping the tissue as described.

Figure 11:
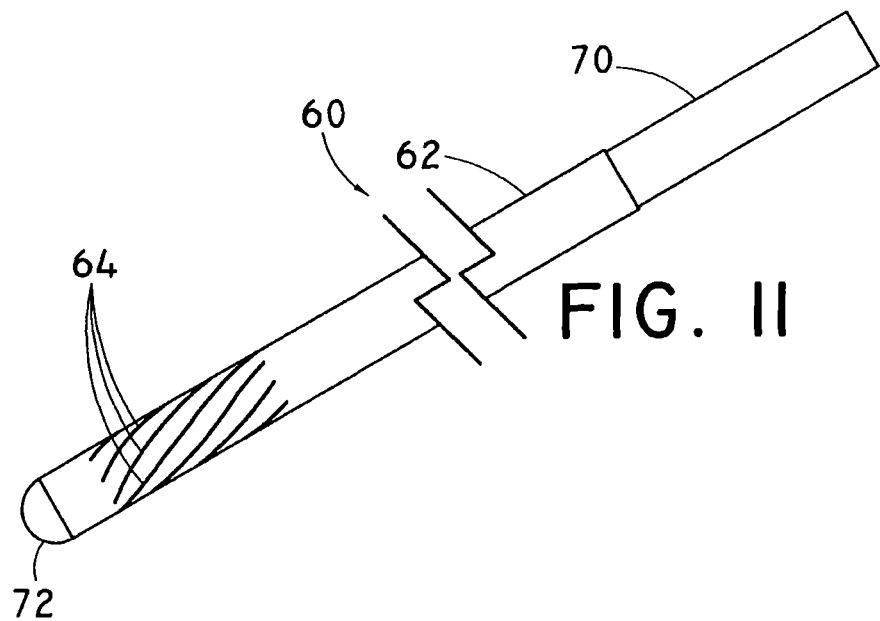
FIG. 11 illustrates an anchor member that may be incorporated into the closure device, shown in a non-expanded condition.
Figure 12:
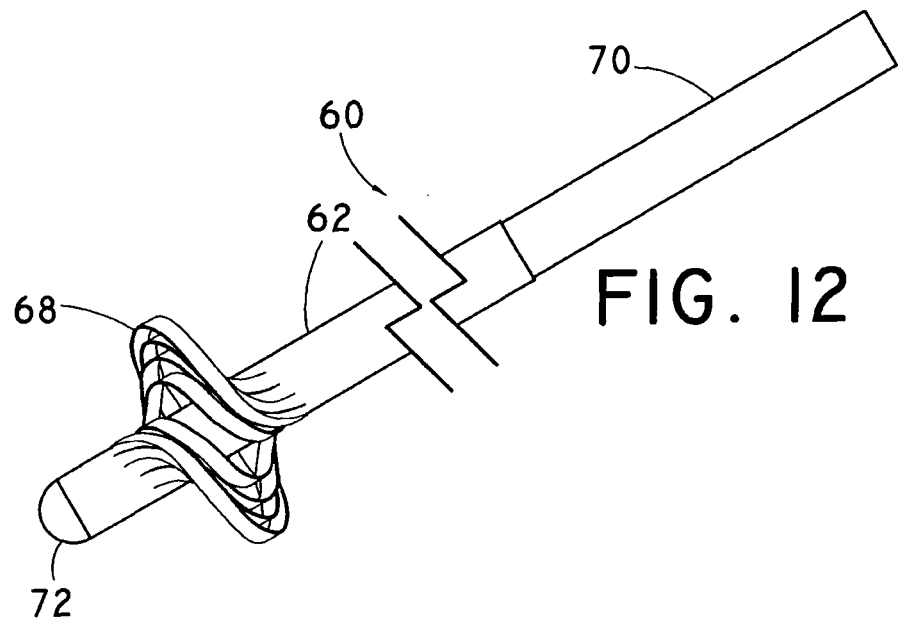
FIG. 12 illustrates the anchor member of FIG. 11, in an expanded condition.

A cut-out portion, such as arc 33, may be cut on each lateral side of a finger. When present, arc 33 provides a space, or reservoir, into which the tissue may fold. In addition, this structure allows more room for an anchor assembly to slide through the fingers when they are in a collapsed condition. The optional anchor assembly is further illustrated, e.g., in FIGS. 11 and 12, and is further described herein.

Figure 3C:
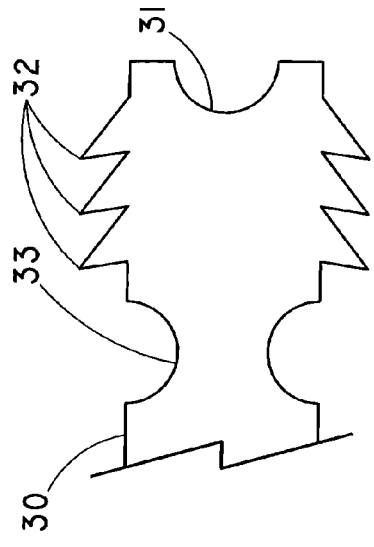
FIGS. 3A-3D are enlarged side views of alternative configurations of the distal portions of the fingers of the grasping member.
Figure 3D:
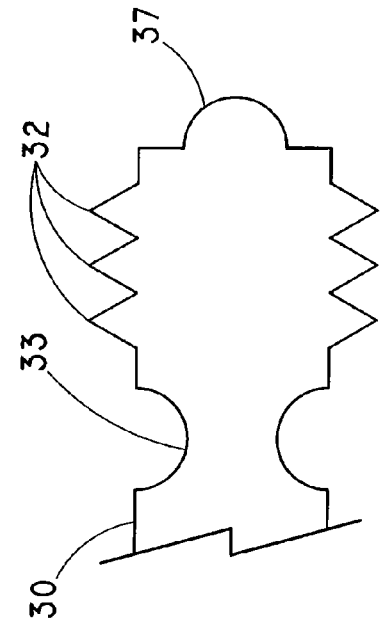
Figure 3A:
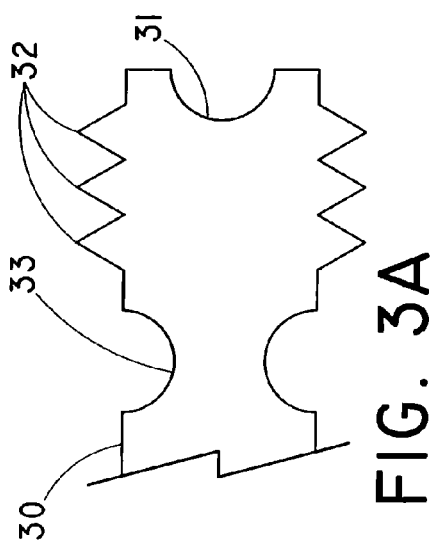
Figure 3B:
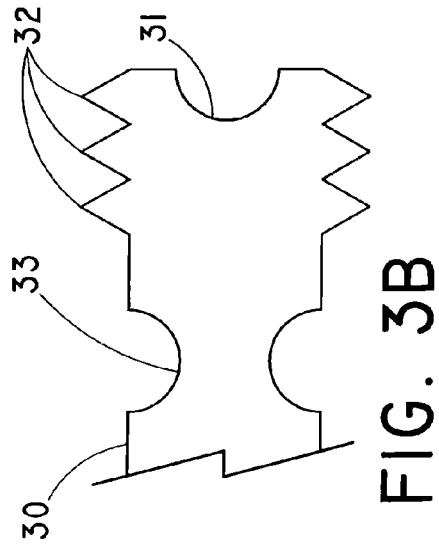

FIGS. 3A-3D illustrate non-limiting examples of various alternative configurations of the distal portions of the grasping member fingers. Each of these figures includes examples of such features. The variations provided in FIGS. 3A-3D are not intended to be exclusive, but rather, to illustrate four possible distal end configurations. Each of these configurations may be preferred for closure of a particular vessel opening. FIG. 3A is an enlarged view of the distal portion of fingers 30 illustrated in FIGS. 3-10. FIG. 3B is similar to FIG. 3A, except that the teeth 32 are moved closer to the distal end of the finger 30. In FIG. 3C, the teeth 32 are tilted in the proximal direction, to function in the manner of barbs. In FIG. 3D, end groove 31 has been replaced with projection 37.

In one preferred embodiment, cut-out portion 31 may have a width of about 0.010 inch (0.25 mm), and a depth of about 0.005 inch (0.13 mm). Teeth 32 may have height of about 0.005 inch (0.13 mm). Arc 33 may have a width of about 0.10 inch (0.25 mm) and a depth of about 0.0035 inch (0.09 mm) length. Projection 37 may have a length (in the distal direction) of about 0.005 inch (0.13 mm).

Some fingers can be provided with one feature, or set of features, whereas other fingers may have other features, or no features. In addition, all fingers 30 need not necessarily have the same length, width, shape, or other dimensions. Preferably, when fingers 30 are of different lengths, teeth 32 will be positioned and aligned along each finger such that the teeth of each finger will correspond in the longitudinal direction with the teeth on an adjacent finger in the manner shown in the figures. However, other arrangements are also possible when the teeth are not so aligned.

Those skilled in the art will appreciate that the number, arrangement, shape, and dimensions, of the fingers, as well as the additional features provided on the fingers, such as features 31, 32, 33, and 37 described hereinabove, are only intended to represent examples of possible arrangements, and are not to be construed as limiting grasping member 22 to any particular structure. For example, additional features may be added to the grasping member 22 to assist in grasping and/or securing tissue surrounding a vessel opening. Additional, or fewer, features may be provided on fingers 30 in a particular case. In addition, not all fingers need have the same arrangement of features. It is believed that one skilled in the art is readily capable of optimizing an arrangement of features for a particular case without undue experimentation.

Following laser cutting of slits 28 as described, and the cutting of grasping features (e.g., features 31-33 in FIG. 2) into fingers 30, the fingers may then be set into a desired shape. This may be accomplished, e.g., by inserting an appropriately shaped conical form (insert) into the distal portion 26.

The assembly comprising the tubular body and conical form is then placed in an oven and heated for an appropriate time, and at an appropriate temperature, to provide the fingers with an internal memory. Thus, when not covered by a sheath, the fingers will have a tendency to expand outwardly from the longitudinal axis of the grasping member, as shown in FIG. 3. The time and temperature required for heating will vary depending on factors such as the composition of tubular body 24, and the dimensions of the fingers. Optimization of these factors is believed to be readily within the expertise of one skilled in the art.

In one preferred embodiment, each finger 30 is shaped such that it includes a segment 30A (FIG. 1) that angles away from the longitudinal axis of tubular main body portion 24. Preferably, segment 30A angles from the longitudinal axis at a predetermined angle, e.g., between about 15 and 60 degrees, and more preferably, about 30 degrees. The particular angle of the fingers of a grasping apparatus from the longitudinal axis will be a function of the shape and dimensions of the particular conical form selected for use, and may be formed based upon an intended use of the closure device. In a preferred embodiment, a more distal segment 30B of the grasping fingers is further angled from the angle described above, as shown in FIG. 4. This enhances the ability of the fingers to grasp the tissue surrounding the vessel opening. When closure device 20 is in use, distal segment 30B may be aligned in one embodiment such that it is substantially perpendicular to the access site. In one preferred embodiment (e.g., FIG. 1), fingers 30 are aligned in a manner such that the respective finger distal tips 34 collectively are arranged in a generally circular manner, wherein the circle has a diameter of, e.g., about 5 mm.

Although distal portion 26 (and therefore fingers 30) of grasping member 22 may be initially formed from the distal portion of tubular main body portion 24 as shown in FIGS. 2 and 3 and described herein, those skilled in the art will appreciate that this is merely one manner in which the distal portion 26 may be formed, and that other constructions may be utilized. For example, distal portion 26 (and fingers 30) may be separately formed, and thereafter securely engaged with the distal end of tubular body portion 24 by any well-known attachment mechanism, such as an adhesive or via mechanical attachment.

Sheath 40 of closure device 20 is preferably formed of a lubricous, relatively rigid tubular material. Non-limiting examples of suitable materials include polyether ether ketone (PEEK), polyamide (nylon), polyimide, polyethylene terephthalate (PET), polysulfone, tetrafluoroethylene (TFE), and fluorinated ethylene propylene (FEP).

As with the grasping member, the precise outer diameter of the sheath 40 is also typically not critical. Preferably, however, such outer diameter will generally be within a range of about 1.5 and 3 mm, such as about 1.7 mm. Sheath 40 includes an inner lumen dimensioned to receive the main tubular (proximal) portion 24 of grasping member 22. Sheath 40 will also preferably have a length such that the proximal end of the sheath 40 extends in the proximal direction beyond the proximal end of the introducer sheath 100, for permitting easy access to the proximal end of the sheath by the user.

During use of closure device 20, sheath 40 is slidable in a distal direction relative to the grasping member 22. FIG. 1 illustrates sheath 40 extending over a portion of the tubular main body 24 of grasping member 22, but not over grasping fingers 30. As a result, fingers 30 are fully radially extended, due to the internal memory set in the fingers as described above.

Figure 4:
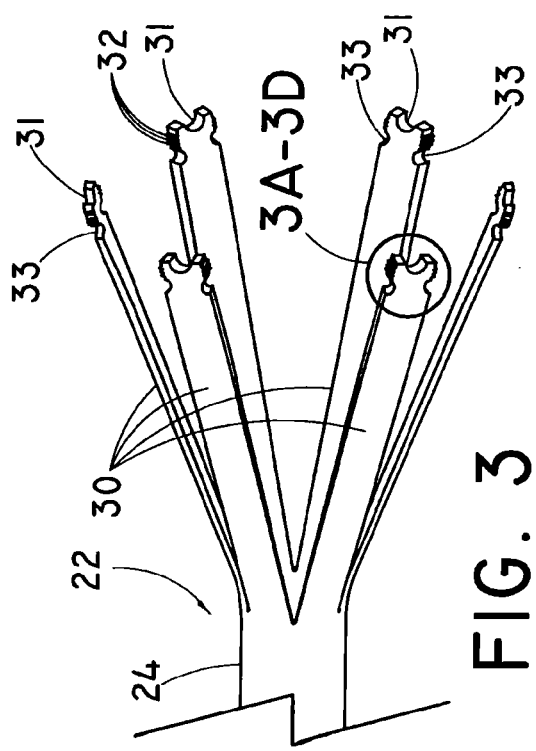
FIGS. 4 and 5 show successive stages of the closure of the device.

In the view depicted in FIG. 4, sheath 40 has been advanced distally relative to grasping member 22, such that a relatively short length (e.g., about 1 mm) of fingers segment 30A is covered by the sheath. This action causes fingers 30 to begin to collapse within the lumen of the sheath 40 from the predetermined angle specified above. In the view depicted in FIG. 5, sheath 40 has been further advanced over fingers 30 such that the sheath encompasses a portion of segment 30B of fingers 30. In this condition, the overlying sheath 40 essentially collapses fingers 30 into a closed position around the vessel opening. In use, the collapsing motion of the grasping fingers pulls, or gathers, the tissue immediately adjacent an opening in a vessel radially inwardly to at least substantially close the access opening, in a manner to be described.

Figure 6:
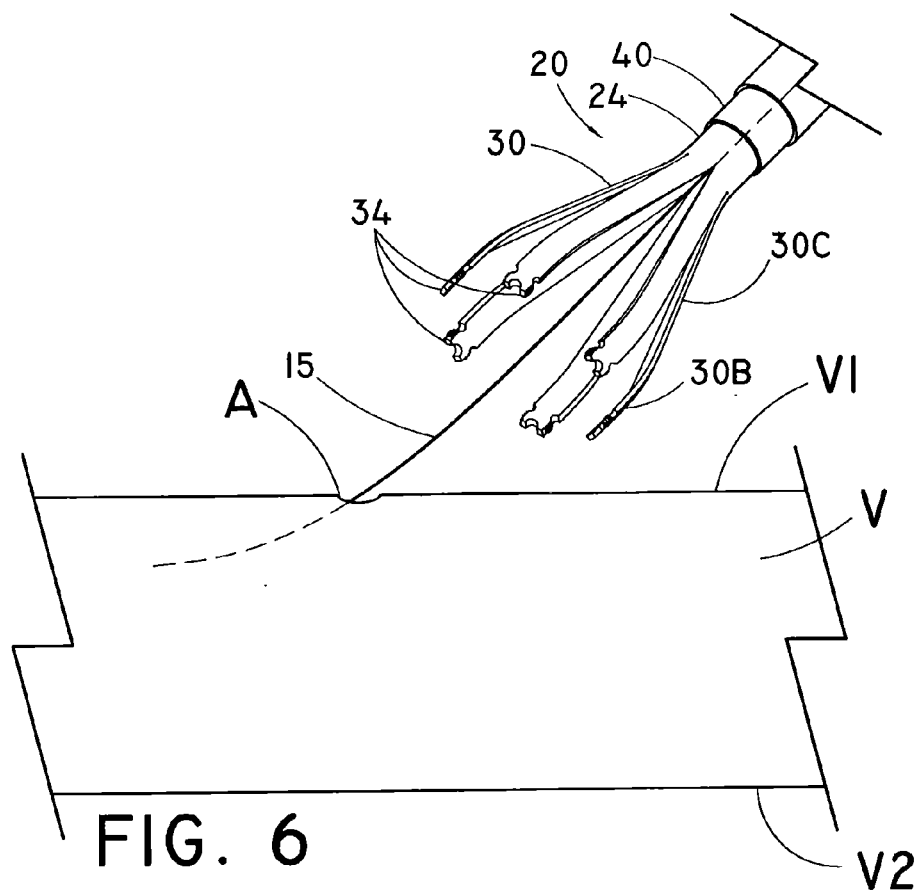
FIGS. 6 and 7 show use of the device to close a vessel opening.
Figure 7:
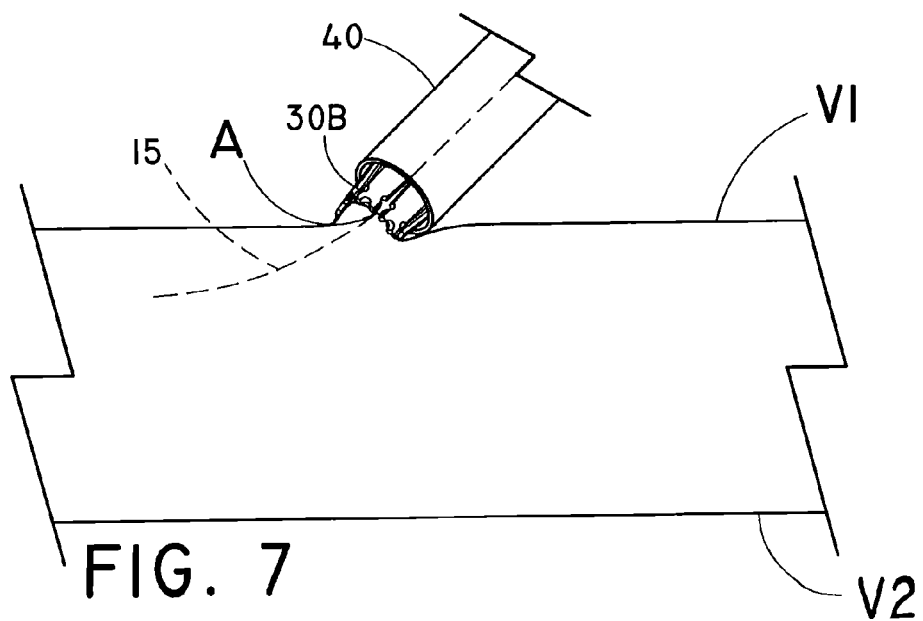

One example of the use of closure device 20 to close an opening A in a vessel V is illustrated in FIGS. 6 and 7. The opening A intended for closure has been made through first vessel wall V1 during the course of a medical procedure that has previously been carried out. The opposite vessel wall is designated in the figures as V2.

As illustrated in FIG. 6, a previously-positioned wire guide 15 has been inserted through opening A into the interior of the vessel by conventional means. Device 20 passes over wire guide 15 such that the respective distal tips 34 of grasping fingers 30 approach the outer wall V1 of vessel V.

As illustrated in FIG. 7, finger distal tips 34 have been further advanced to grasp the outer surface of vessel wall V1, and sheath 40 has been advanced over fingers 30 to collapse the fingers as shown. In this view, fingers 30 collapse in a manner such that finger segments 30B grasp, or gather, the tissue surrounding vessel opening A. When features, such as features 31-33 are included on fingers 30, tissue may be gathered between the fingers as described. When the fingers are collapsed as shown, the tissue surrounding the vessel opening is brought together in a manner such that the vessel opening is at least substantially closed. Once the tissue has been gathered as described, the fingers can maintain contact with the site to allow clotting and wound sealing to take place.

Figure 5:
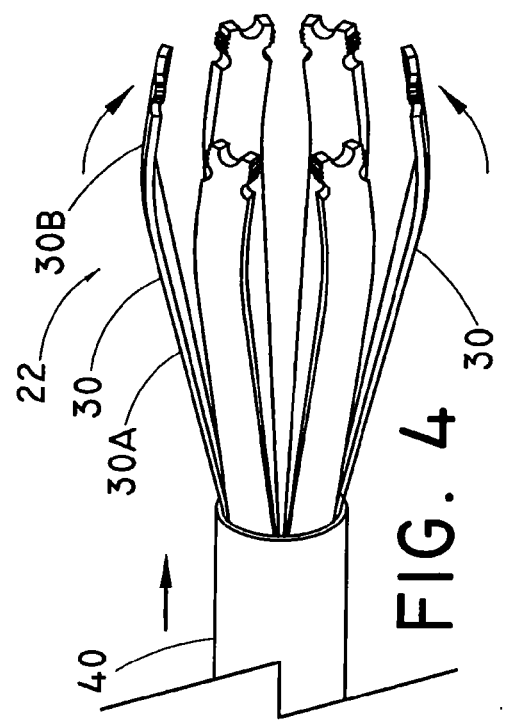

FIG. 8 illustrates a variation of the closure device of FIG. 1. In this variation, a skirt 39 is provided around at least a portion of fingers 30 of closure device 20. Preferably, skirt 39 also extends along a length of tubular main body portion 24. In the version shown in FIG. 8, skirt 39 extends around the outer surface of fingers segment 30A (FIG. 1), and does not extend along segment 30B. Skirt 39 comprises an expandable material, such as ePTFE, a polyether block amide, polyisoprene or silicone, that is capable of expanding as fingers open radially as shown in FIG. 8. Skirt 39 prevents surrounding tissues from getting caught between the upper part (e.g., segment 30A) of fingers 30, and thereby preventing closure of the fingers, as shown in FIGS. 5 and 7.

Although FIG. 8 illustrates the presence of skirt 39 around the outer surface of the fingers, the skirt can alternatively be positioned around the inner surface of the fingers. As still another alternative, a separate skirt can be provided around each of the outside and inside of the fingers. As yet another alternative, the skirt may extend further toward the distal end of the fingers than shown in FIG. 8.

Additional variations that may be made to the grasping member 22 are illustrated in FIGS. 9 and 10. On some occasions it may be desirable to allow the main tubular body portion 24 of the grasping member 22 to bend, or articulate, as the distal end of closure device 20 approaches a vessel opening intended for closure. This bending, or articulating, ability may facilitate the positioning of the closure device relative to the opening, and thereby facilitate grasping of a particular tissue segment surrounding the opening.

FIGS. 9 and 10 illustrate two possible ways in which this bending or articulation may be accomplished. In FIG. 9, a spiral slot 41 is formed along a discrete length of tubular member 24. Spiral slot 41 weakens the length of the tubular member 24 to permit a degree of bending of the tubular member as may be desired. In FIG. 10, a helical coil 42 is formed along a discrete length of tubular member 24. Coil 42 may be formed to have any tension requirements desired for permitting a desired degree of bending of the affected tubular member length 24.

Preferably, the slot 41 or coil 42 will only extend along, or interrupt, the tubular member for a sufficient length, e.g., about 2 mm to 2 cm, to enable bending of a discrete length of the tubular member. Those skilled in the art will appreciate that the spiral slot 41 and coil 42 illustrated herein are only examples of well-known structures that may be utilized for bending a shaft member as described, and that other structures capable of allowing bending or articulation may be substituted for the spiral slot and coil as shown.

Another embodiment of the closure device is illustrated in FIGS. 11-14. In this embodiment, an anchor 60 is provided for facilitating the wound closing. In one form, anchor 60 is formed from a cannula 62 having a series (such as 8) of generally helical or spiral slits 64 laser cut or otherwise formed along the distal end of the cannula. Preferably, cannula 62 is formed from a relatively rigid biocompatible tubular structure, such as a metal, metal alloy, or relatively rigid polymeric tube. Nitinol or other spring type metals are particularly preferred materials for forming cannula 62.

In the embodiment shown, anchor 60 includes a rod 70 or like structure that extends through the lumen of cannula 62. A distal end 72 of rod 70 extends beyond the distal end of cannula 62, and is fixedly attached thereto, e.g., by welding. When the operator advances the cannula in the distal direction relative to the rod (FIG. 12), the spiral slits 64 bow radially outwardly to form a generally large diameter anchored portion 68. Large diameter portion 68 may be maintained as long as cannula 62 is maintained in the distal position relative to rod 70. When cannula 62 is released, or otherwise moved in a proximal direction relative to rod 70, spiral slits 64 substantially re-seat to the position shown in FIG. 11.

Figure 13:
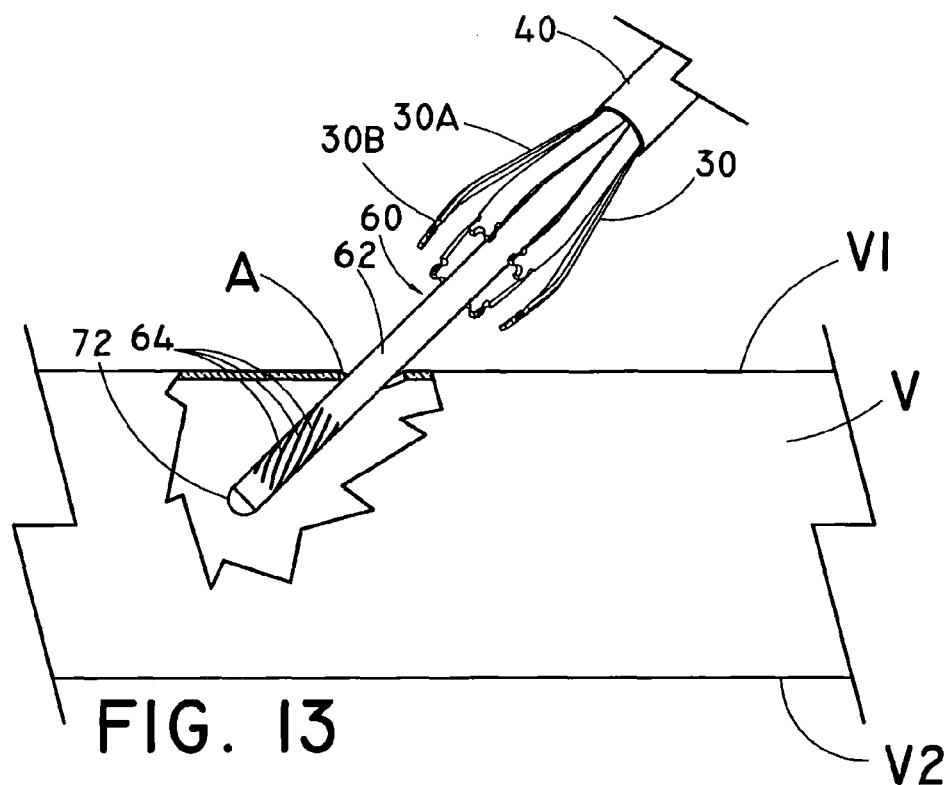
FIG. 13 illustrates the anchor member in combination with the closure device, wherein the distal portion of the anchor member is introduced through the vessel opening while in a non-expanded condition.

FIG. 13 illustrates closure device 20 in combination with optional anchor 60. As grasping fingers 30 approach opening A, the distal portion of anchor 60 is passed through a central passageway of the closure device. Slits 64 extend through opening A, and into the interior space of the vessel. The cannula is urged distally relative to the rod, such that spiral slits 64 bow outwardly to form large diameter anchor portion 68, as described above.

Figure 14:
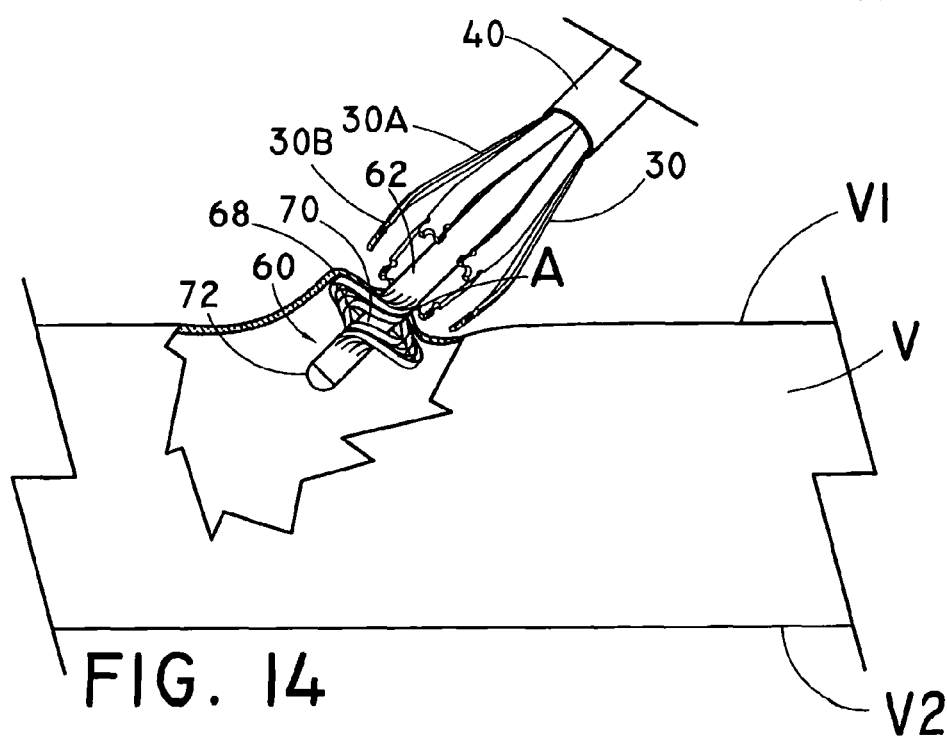
FIG. 14 illustrates the anchor member in combination with the closure device as shown in FIG. 13, wherein the distal portion of the anchor member is shown in an expanded condition.

The presence of large diameter portion 68 within the interior space of the body vessel forms a platform within the interior space of the body vessel. The tissue surrounding the access opening may be aligned on this platform, and manipulated in a manner to provide a suitable surface for receiving the distal tips 34 of fingers 30, as shown in FIG. 14. This arrangement provides the grasping fingers with leverage that assists in closing the wound.

Those skilled in the art will appreciate that other conventional structures having a distal segment capable of radial expansion may be substituted for the particular arrangement of the cannula and rod described above. For example, the anchor member may comprise an expandable balloon, such as a Fogarty balloon. In this case, the balloon is capable of being inserted into the interior of the vessel in a non-expanded condition, and expanded therein to have a larger diameter expanded portion.

Figure 15:
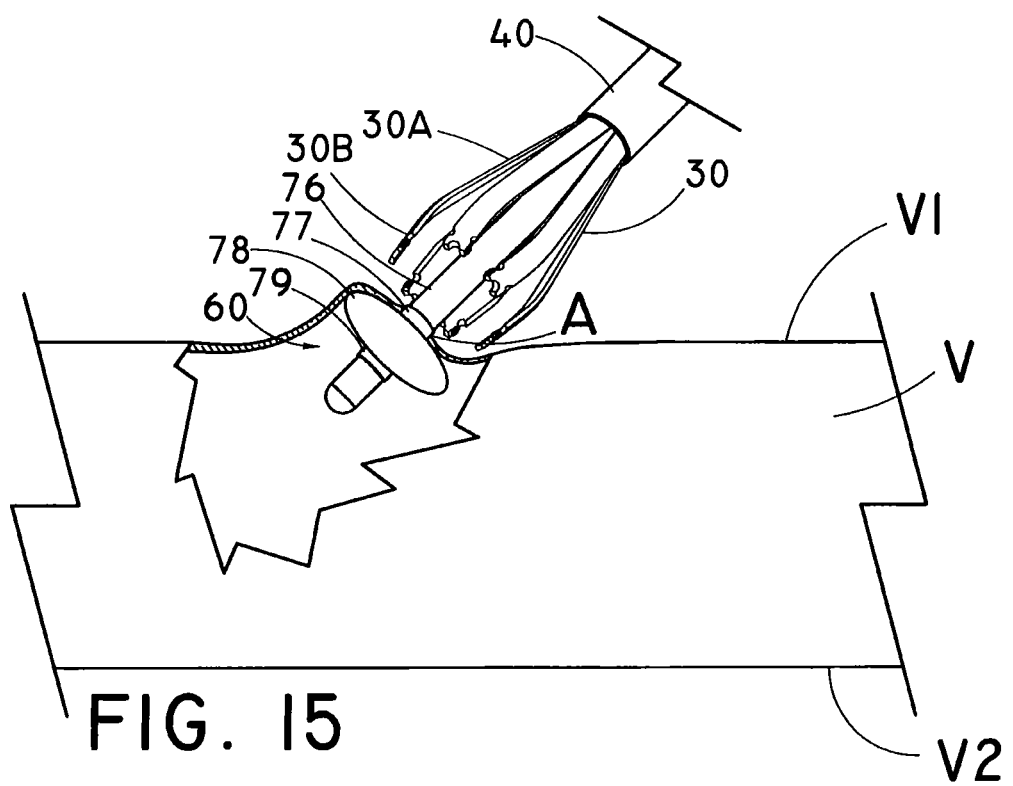
FIG. 15 illustrates use of an expandable balloon as the anchor member.

One non-limiting example of a balloon anchor is illustrated in FIG. 15. The balloon anchor includes a shaft portion 76 and an expandable balloon 78. Balloon 78 includes a proximal end 77 and a distal end 79 in sealing engagement with shaft portion 76 in well-known fashion. Shaft portion 76 communicates with a source of inflation fluid (not shown), and with the interior of balloon 78, in conventional manner for transmitting the fluid into the balloon interior upon inflation of the balloon. Those skilled in the art will appreciate that suitable balloons for use herein may have other expanded geometrical configurations, such as spherical, cylindrical, etc. Expandable balloons are in widespread use in the medical arts, and those skilled in the art can readily select an appropriate balloon for use herein.

Once the tissue surrounding the opening has been grasped and positioned for closure as described hereinabove, the grasping apparatus 20 can maintain contact with the site for a sufficient time to allow clotting and wound healing to occur. It is envisioned that such contact may take approximately 10-30 minutes for sufficient clotting and/or wound healing to occur such that the grasping apparatus can be removed from the access site. Those skilled in the art will appreciate that lesser, or greater, time periods may be appropriate in a particular case.

As an alternative to maintaining continual contact as described above to allow clotting and wound healing to occur, the opening at the access site can be cauterized by applying an electrical current to the site while the closure device is still in place. In this embodiment, an insulator (such as sheath 100) may be applied around a portion of the closure device 20 to protect the surrounding tissue, and an electrosurgical generator 80 may be electrically engaged with the closure device. One non-limiting example of the electrical connection of the optional electrosurgical generator is shown schematically and in phantom in FIG. 8. Those skilled in the art will appreciate that the electrosurgical generator unit could also be included with any of the other embodiments illustrated and/or described herein.

By incorporating the electrosurgical unit 80, electrical current can be passed through the grasping fingers 20 for transmission to the tissue surrounding the access opening. The use of RF current is known in the medical field to be useful for such purposes as resection, coagulation and hemostatic sealing of body openings, such as vessel openings, in both open and laparoscopic surgery. Electrosurgery can be used to cut, coagulate, dessicate, or fulgurate tissue. Among others, its benefits include the ability to make precise cuts with limited blood loss. In this case, the RF current electro-cauterizes the vessel access site to close the opening in well-known manner.

As well known by those skilled in the art, units for generating electrical (e.g., RF) current typically include an electrode and a ground plate. The generated RF current travels from the electrode tip to the access site, and back to the unit via the ground plate. The use of the RF current in this manner promotes faster healing and recovery time. Suitable electrosurgical equipment to carry out such techniques may be obtained commercially at www.boviemedical,com, among other sources.

Another feature of the invention involves the use of a bioabsorbable grasper, or clip, for closure of an opening in a body vessel. Non-limiting examples of such bioabsorbable graspers are shown in the following figures.

One embodiment of a bioabsorbable grasper 200 is illustrated in FIGS. 16A-16B. In this embodiment, bioabsorbable grasper 200 comprises a grasping member 202, and a closing member 220, such as a ring, sized to be received over a portion (e.g., the proximal portion in FIG. 16A) of grasping member 202. An optional anchor 225, similar to any of the anchors described and illustrated above (e.g., FIG. 13) may be provided for facilitating closure of the vessel opening.

Preferably, both of grasping member 202 and closing member 220 are formed from bioabsorbable or biodegradable materials, hereinafter called bioabsorbable materials. If desired, closing member 220 may also include a Shish-type (expandable foam) material.

Those skilled in the art are aware that such bioabsorbable materials are composed and configured to degrade or dissolve over time when exposed to body tissue and/or fluids. These materials may be made from one or more bioabsorbable polymers in varying combinations, such as polymers, copolymers, and block polymers. A non-limiting listing of bioabsorbable (i.e. bio-resorbable/biodegradable) polymers suitable for use herein includes poly-lactic acid, polyglycolic acid, polyglycolides, polylactides, co-polymers of polyglycolides and polylactides, polycaprolactones, polyglycerol sebacate, polycarbonates (e.g. tyrosine derived polyethylene oxide), polybutylene terephthalate, polydioxanones, hybrids, composites, collagen matrices with growth modulators, polyanhydrides, polyorthoesters, chitosan, aliginates, proteoglycans, glycosaminoglycans, vacuum formed SIS (small intestinal submucosa), fibers, chitin, and dextran. The bioabsorbable polymers may be used alone or in combination with these or other bioabsorbable polymers in varying compositions. Typically, rigid or semi-rigid bioabsorbable materials will be preferred herein. Examples of bioabsorbable materials exhibiting rigid characteristics include chitosan, alginates, and co-polymers of polyglycolides and polylactides. Examples of bioabsorbable materials exhibiting stretchable characteristics include co-polymers of polycaprolactone with polyethylene, polypropylene, polyamides, or polyester. A 10:90 lactide:glycolide (PLG) and a 20:80 PLDL are particularly preferred compositions. Those skilled in the art will appreciate that the compositions listed hereinabove are only examples of suitable bioabsorbable materials that are suitable for use herein, and that other suitable compositions known in the art for such purposes may be substituted for those specifically listed hereinabove.

If desired, grasping member 202 may be formed in the same general manner as grasping member 22 described above, such that grasping member 202 includes a tubular main body portion 204, and a distal portion 206 extending in a distal direction therefrom. Tubular main body portion 204 of the grasping member 202 can be provided with a larger diameter portion or similar structure in the vicinity of the distal end to act as a stop for closing member 220, thereby preventing the closing member from advancing any further than desired in the distal direction. The grasping member can include a central passageway extending therethrough for receiving a wire guide and/or any of the various embodiments of the anchors described herein.

Tubular main body portion 204 may have a generally circular cross section, although tubular body members having other geometrical cross sections, such as an elliptical, rectangular, etc., may alternatively be utilized. Main body portion 204 can have a proximal end 205 that is configured to be releasably attached to another member as described herein. In one example, the proximal end can be a larger diameter proximal end, such as a bead shown in FIGS. 16A-16B. Distal portion 206 can be provided with a plurality of fingers 210. Fingers 210 are movable between an open position (FIG. 16A), which the fingers are generally biased to, and a closed position (FIG. 16B). Closing member 220 may facilitate the movement of the fingers to the closed position. For example, closing member 220 can be moved between a first position that is somewhere along main body portion 204 and a second position where the fingers are urged to the closed position. In FIG. 16B, the first position is shown as C in a dashed line, and the second position is shown as D, which can be somewhere along the fingers as shown in FIG. 16B.

One or more outward protrusions 215 can be provided along fingers 210, preferably along an outer surface of the fingers. Protrusion 215 is configured to inhibit the movement of closing member 220 in the proximal direction, the distal direction, or both directions, once closing member 220 is at its second, locking position. The protrusions may lock the closing member in its second position so that the closing member is in a fixed position. Preferably, a pair of protrusion are provided along at least one finger 210, and spaced apart just enough to receive closing member 220. Multiple pairs of protrusions along the fingers can cooperate to define an annular channel, as shown in FIG. 16B. The finger surface between the protrusions may even be recessed below the general outer surface of the finger that surrounds the protrusions, so that the protrusions define walls of the recess.

A proximal protrusion 215A can be shaped so that closing member 220 can move easily across proximal protrusion 215A in the distal direction. Proximal protrusion 215A can be further shaped so that the closing member is inhibited from moving across the proximal protrusion in the proximal direction. A distal protrusion 215B can be shaped so that closing member 220 is inhibited from moving across distal protrusion 215B in a distal direction. For example, proximal protrusion 215A can have an oblique surface 216 extending obliquely from the surface of the finger in the outward direction to the outer edge of the protrusion. Distal protrusion 215B can have an abrupt surface 217 extending substantially perpendicular to the surface of the finger in the outward direction. Proximal protrusion 215A may also have an abrupt surface 218 extending in a similar manner. The pair of protrusions 215A, 215B can define a predetermined second position of closing member 220 so that the operator is ensured that grasping member 202 is in the closed position and should not move from that position under normal operating conditions. Tactile feedback may also be provided to the operator in the form of vibration and/or sound of a "click" to ensure the closing member is locked between the protrusions. The locking of the closing member can prevent the closing member from being pushed too far in the distal direction, even off of the fingers, making the grasping member inoperable to close the vessel opening. This locking can further inhibit the closing member from moving away from the locking position in the proximal direction, which can prematurely allow the grasping member to lose its engagement with the vessel wall before sufficient healing of the vessel opening.

As appreciated by those skilled in the art, a protrusion does not have to be positioned on the fingers as shown in FIG. 16A; a protrusion may be positioned on the closing member 220. For example, a protrusion may be positioned along the inner surface of the passageway of the closing member 220, such as a series of bumps or an inner ring member, which can be engageable with a recess formed on the outer surface of the finger 210. Instead of, or in addition to, having a protrusion, like in FIG. 16A, the finger 210 may include a recess or groove formed into the surface the finger and sized to receive the axial width of the closing member 220. The walls of the groove can have the abrupt surface 217 of protrusion 215. Further, the closing member 220 may have a recess or groove along its inner surface of the passageway, which is engageable with a protrusion of the fingers. To this end, the protrusions need not surround the closing member, such as shown in FIG. 16B, but may be inserted into the groove along the closing member. Other arrangements as known by one skilled in the art of grooves and protrusions can be used for mechanical coupling between the closing member and the fingers to facilitate fixed positioning of the closing member relative to the fingers.

Fingers 210 may be formed in the same general manner as fingers 30. Thus, for example, a series of slits 211 (e.g., 6) may be cut, e.g., by laser cutting, along the length of distal portion 206, and shaped as described above with any of the aforementioned bioabsorbable materials. Alternatively, grasping member 202 can be formed by other known processes, such as molding using "micro-molding" techniques. When molded, the fingers will typically be molded into an "open" condition, such that they are closeable upon distal movement of the closing member, as described herein. Generally speaking, fingers 210 may be shaped similar to fingers 30, and may include features, such as one or more of features 31, 32, 33, shown as 212, 213, 214, respectively. For example, the fingers 210 can have a cross-section of any shape, shown as a rectangular cross-section, defined by a pair of lateral sides 221, a radial outer surface 222, and a radial inner surface 223. Accordingly, teeth 213 may be positioned along at least one of the lateral sides 221, cut-out portion 214 may be positioned along at least one of the lateral sides 221 proximal of the teeth 213, cut-out portion 212 may be positioned along the distal end of the finger. If desired, fingers 210 may also be molded or otherwise shaped such that they include portions similar to portions 30A and 30B of fingers 30, shown as 210A and 210B in FIG. 16A, respectively. Those skilled in the art will appreciate that other known processes may be used to form bioabsorbable grasping member 202. Protrusions 215 may be molded as part of the finger, or may be individually attached to the fingers, as appreciated by those skilled in the art.

Figure 17:
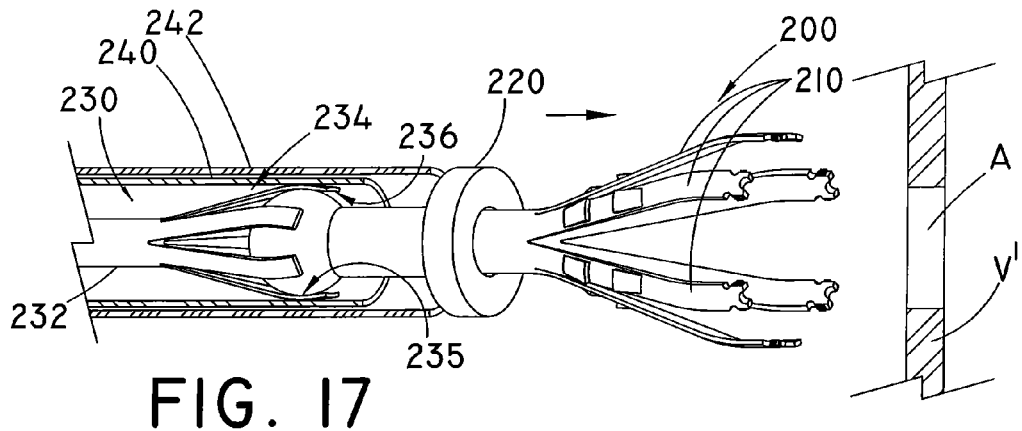
FIGS. 17-19 illustrate operation of the grasper of FIG. 16A.
Figure 18:
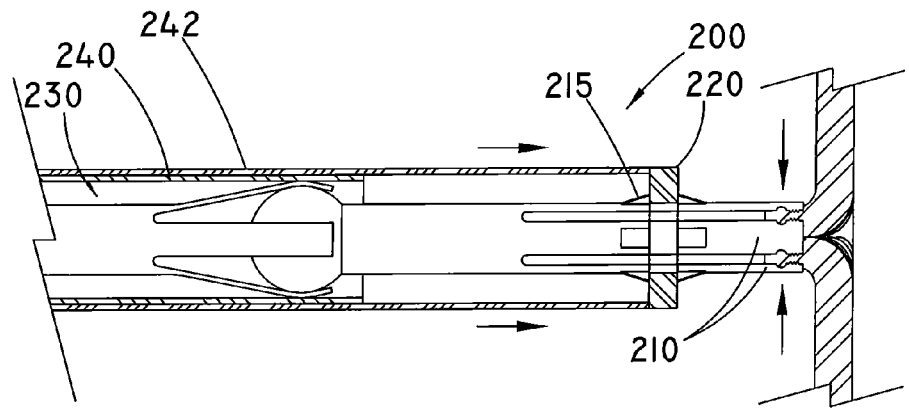
Figure 19:
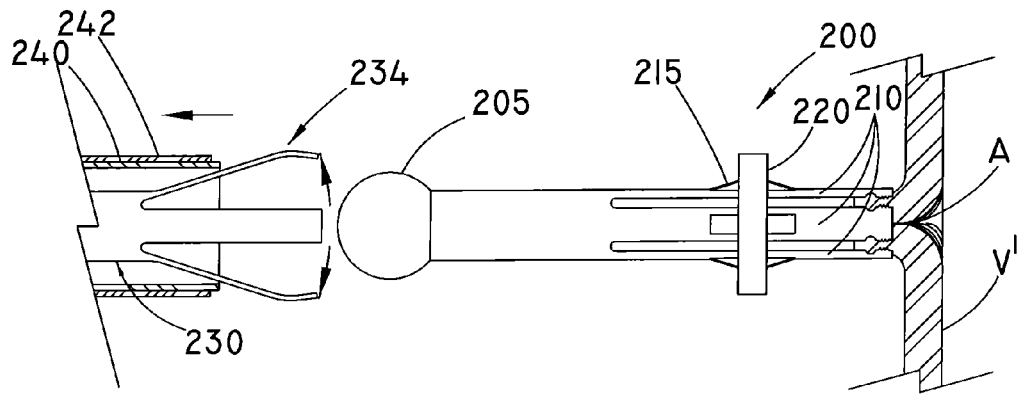

One manner in which grasper 200 may be used is shown in FIGS. 17-19. In FIG. 17, a detachable arm 230 can be removably attached to grasper 200. If desired, detachable arm 230 may be formed in the same general manner as grasping member 22 described above, such that detachable member 230 includes a tubular main body portion 232, and a plurality of fingers 234 extending in a distal direction therefrom. Generally speaking, fingers 234 need not be shaped similar to fingers 30 with the one or more of features 31, 32, 33. Instead, a portion 235 of the inner surface 236 of fingers 234 can be configured with frictional enhancements, such as surface irregularities such as from machining or etching, or a soft durometer material layer such as an elastomer or silicone. Detachable arm 230 is advanced relative to grasper 200 such that fingers 234 of detachable arm 230 are positioned over beaded proximal end 205 of grasper main body portion 204. Preferably, frictional portion 235 is placed in engagement with the beaded proximal end 205. A sheath 240 (such as sheath 40) is advanced in the distal direction to close fingers 234 of detachable arm 230 over the beaded proximal end 205, thereby locking the detachable arm in place. Sheath 240 can have a luminal diameter sized to move fingers 234 radially inward in order to apply a radially compressive force around a portion of the grasping member, or preferably around beaded proximal end 205, so that inner surface 236 of the fingers are in frictional contact with the beaded proximal end. At this time, fingers 210 of grasper 200 are still in the open position.

Once the finger distal tips of grasper 200 engages the outer surface of the vessel wall V1, the tissue surrounding the vessel opening A, sheath 240 can be further configured to engage and move closing member 220 to the second position, thereby locking the closing member in place and closing fingers 210. The closing fingers 210 can bring the tissue surrounding the vessel opening together in a manner such that the vessel opening is at least substantially closed as described herein. Alternatively, in FIG. 18, a second sheath 242, instead of sheath 240, may be used to advance the closing member to the second position. Second sheath 242 can have a luminal diameter that is sized to slidably fit around the outer surface of sheath 240. In FIG. 19, closing member 220 is in the second position, thereby bringing the tissue surrounding the vessel opening A together in a manner such that the vessel opening is at least substantially closed. When used, second sheath 242 can then be withdrawn in the proximal direction away from grasper 200. Sheath 240 is then withdrawn from fingers 234. This withdrawal can allow fingers 234 of detachable arm 230 to move to the open position away from frictional contact with the beaded proximal end 205. The detachment of the detachable arm from the grasping member can be without any additional manipulation of the detachable arm, such as from tugging, twisting, jiggling or the like the detachable arm, or without additional steps, such as removing the wire guide, cutting, or waiting for dissolving of an adhesive or material. Detachable arm 230 is then withdrawn from grasper 200, thereby leaving the grasper in the body. The access site from the patient's skin can then be closed or sealed as appreciated by those skilled in the art. An introducer sheath (not shown) may be used to facilitate placement of the grasper, the detachable arm, the sheath, and the second sheath (when used) at the vessel opening.

Figure 20A:
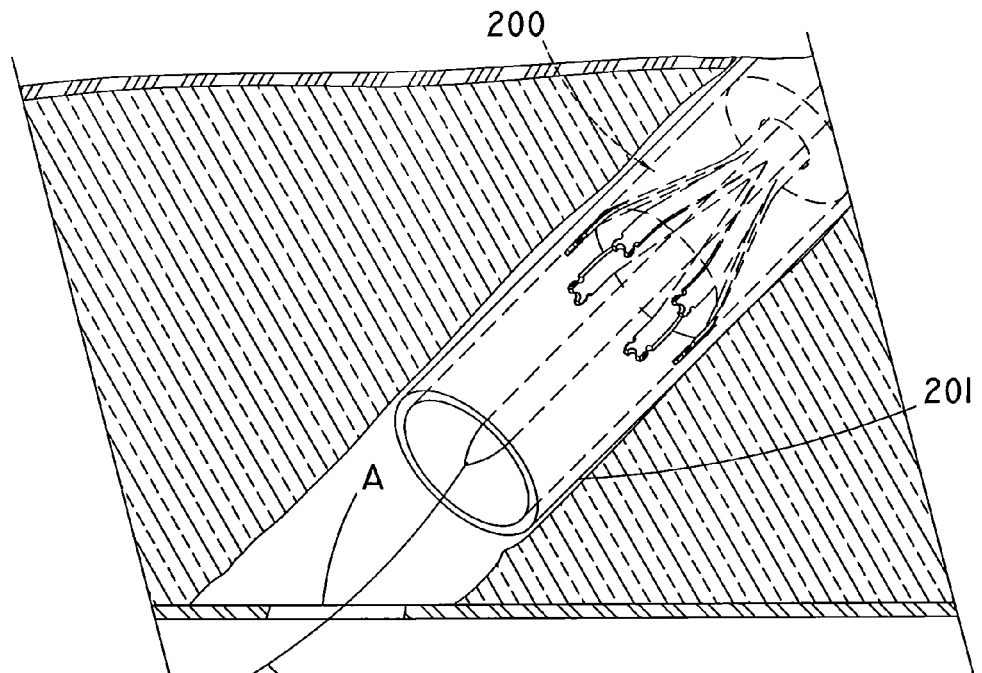
FIGS. 20A-20D illustrate use of the grasper of FIG. 16A in closing an opening in a vessel wall.
Figure 20B:
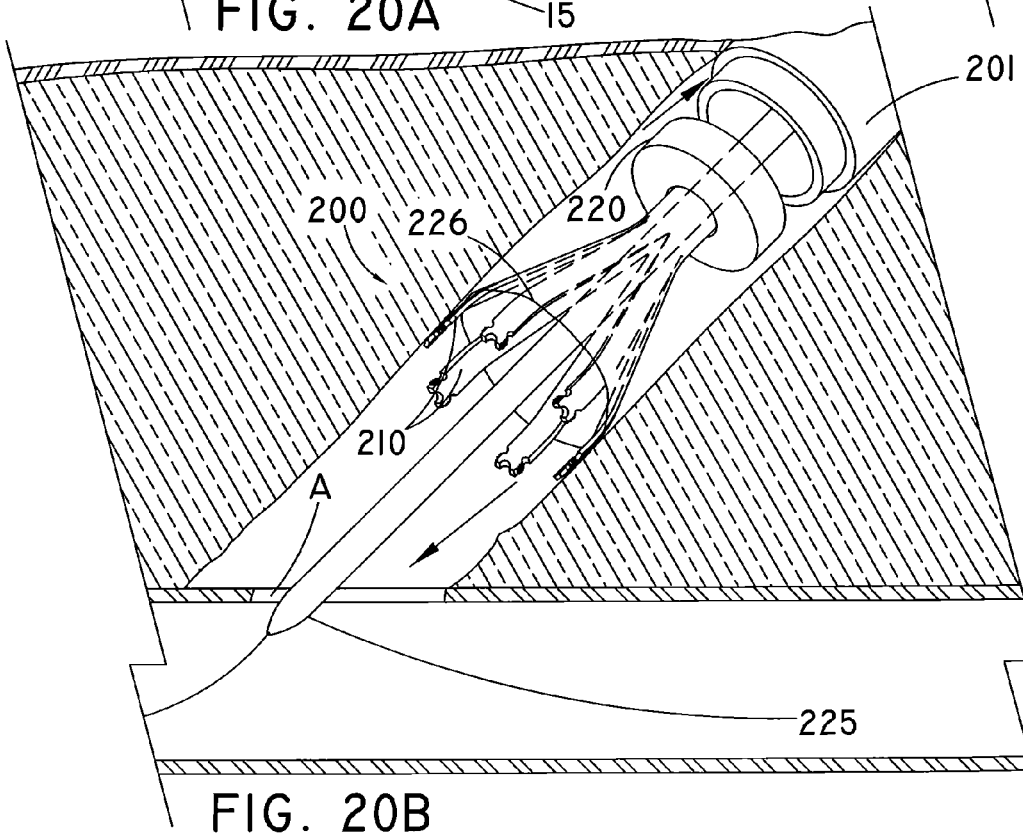

FIGS. 20A-20D illustrate one manner in which grasper 200 may be used for closing an opening A in a vessel wall. In FIG. 20A, an introducer sheath 201 containing grasper 200 in introduced to the opening A, which can be over a wire guide 15 that has previously been inserted into the vessel through the opening. Preferably, grasper 200 is advanced toward the opening at an angle as shown. In FIG. 20B, the introducer sheath 201 can be withdrawn from the grasper to allow the fingers to move to the open configuration. According to this example, grasper 200 also includes optional anchor 225, such as any of the anchor mechanisms described and illustrated above (e.g., FIG. 13) and an optional skirt 226 such as the skirt described and illustrated above (e.g., FIG. 8). As grasping fingers 210 approach opening A, the distal portion of the optional anchor is passed through a central passageway of the closure device in the manner described above.

Figure 20C:
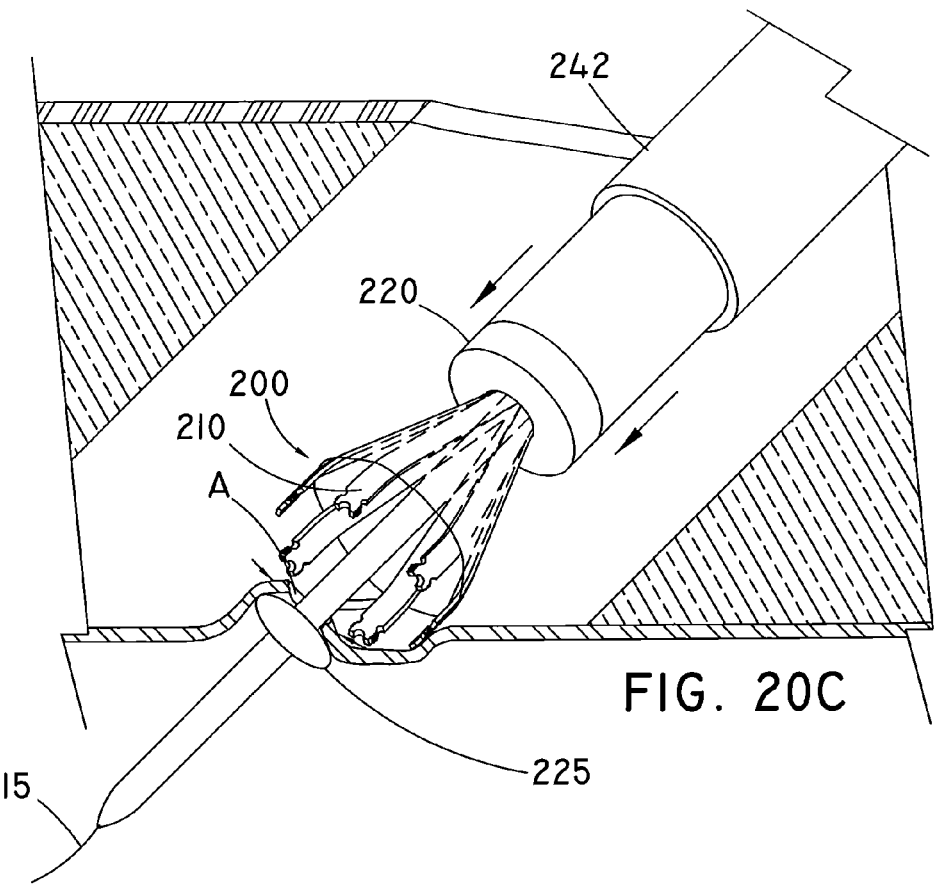
Figure 20D:
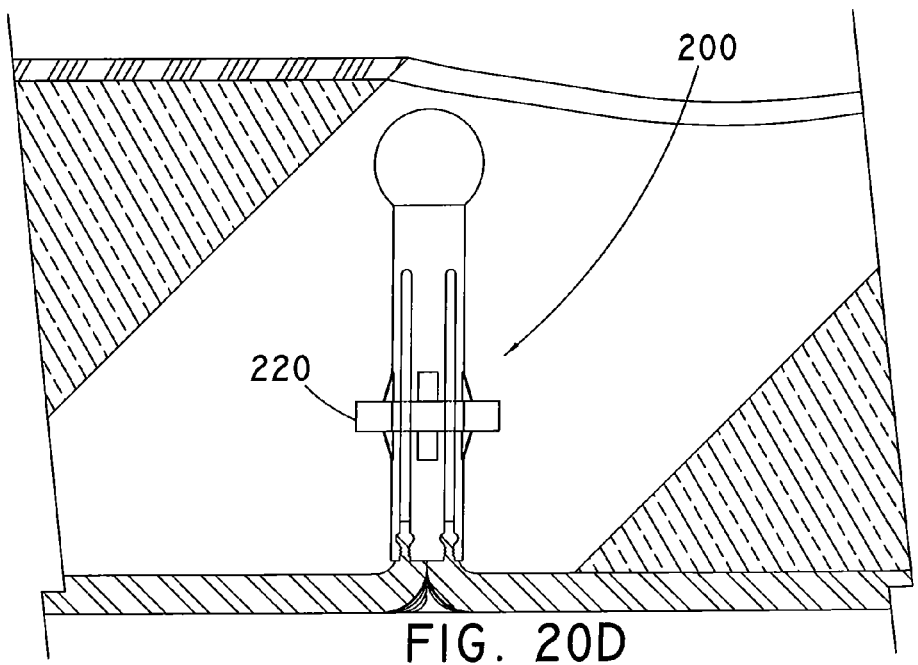

In FIG. 20B, fingers 210 are further advanced distally until they generally surround opening A, in the manner described previously hereinabove. This is also shown in FIG. 24A. In FIGS. 24A-24D, the grasper may be advanced in generally perpendicular fashion to the opening. It is preferred, however, that grasper 200 is advanced at an angle as shown in FIG. 20A. In FIG. 20C, closing member 220 is advanced distally (e.g., with a sheath in the manner described above with reference to FIGS. 18 and 19) to close fingers 210 around the opening A. Once the fingers 210 are closed around opening A, the portions of the vessel wall surrounding the opening are brought together in a manner to close, or at least substantially close, the opening. At this time, the sheath for moving the closing member may be retracted in the proximal direction. The detachable arm (such as detachable arm 230) may then be detached from grasper 200 by reversing the actions of FIGS. 17-19 and the wire guide 15 removed, thereby leaving the bioabsorbable grasper in position closing the vessel opening, as shown in FIG. 20D. Since the grasper is bioabsorbable, it need not be later removed by the physician.

Figure 21B:
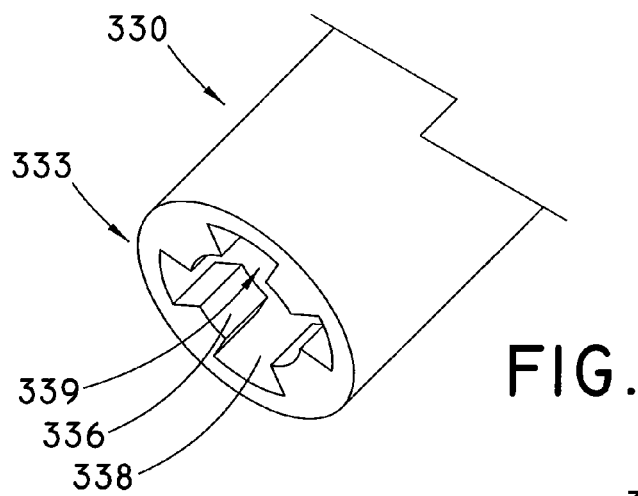
FIGS. 21A-21E illustrate another embodiment of a grasper.
Figure 21A:
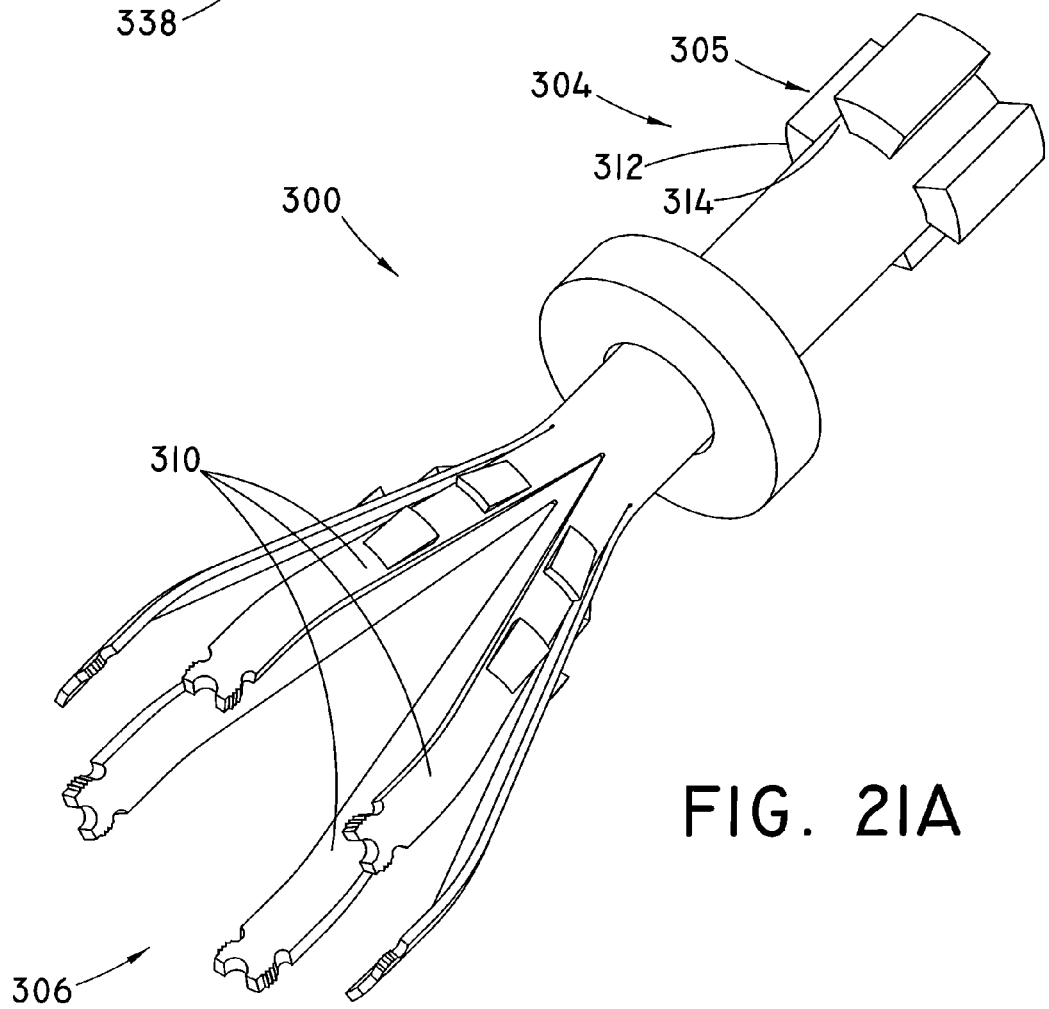
Figure 21C:
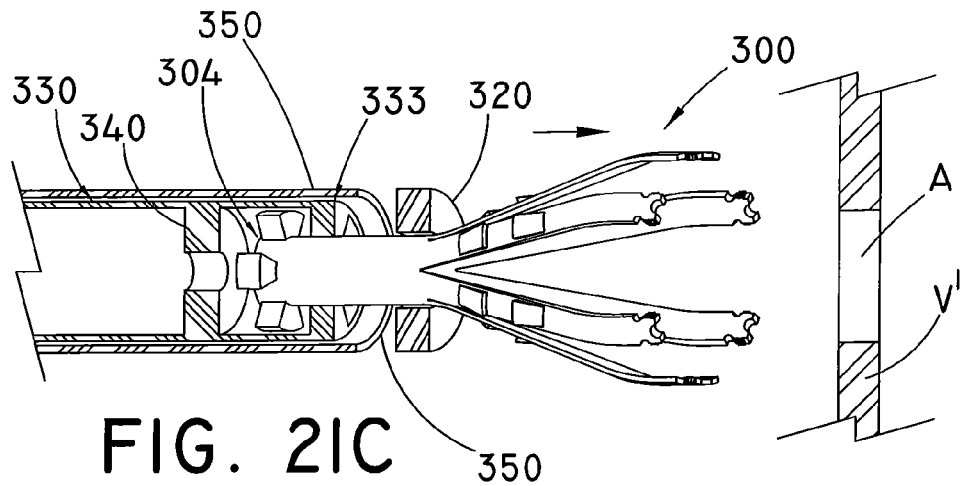

FIGS. 21A-21E illustrate another embodiment of a bioabsorbable device for closure of an opening in a vessel. In this embodiment, grasper 300 includes a distal portion 306 having fingers 310, in a manner generally similar to those of grasper 200 described above. In this case, proximal body portion 304 is provided with a keyed structure, such as alternating ribs 312 and grooves 314 that extend to the proximal end 305 as shown. A detachable arm 330 can be structured in complementary fashion with proximal body portion 334, such as with ribs 336 and grooves 338, as best shown in FIGS. 21B-21C. Detachable arm 330 can include a tubular body with a keyway structure with ribs 336 and grooves 338 arranged within a lumen 339 at a distal portion 333 of the detachable arm. A physical stop 340, such as a ring, can be provided within lumen 339 of detachable arm 330 to inhibit axial movement of proximal body portion 304 of grasper 300 in the proximal direction. As appreciated by those skilled in the art, the detachable arm may include the keyed structure as shown on the grasper 300, and the grasper may include the keyway structure as shown on the detachable arm 330.

Figure 21D:
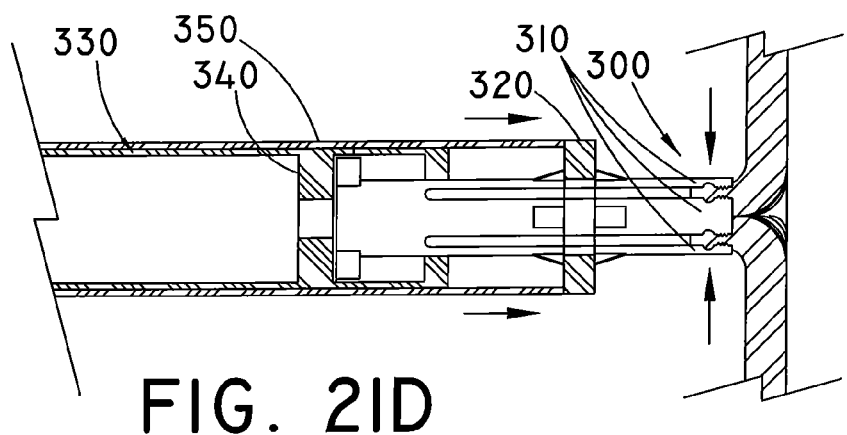
Figure 21E:
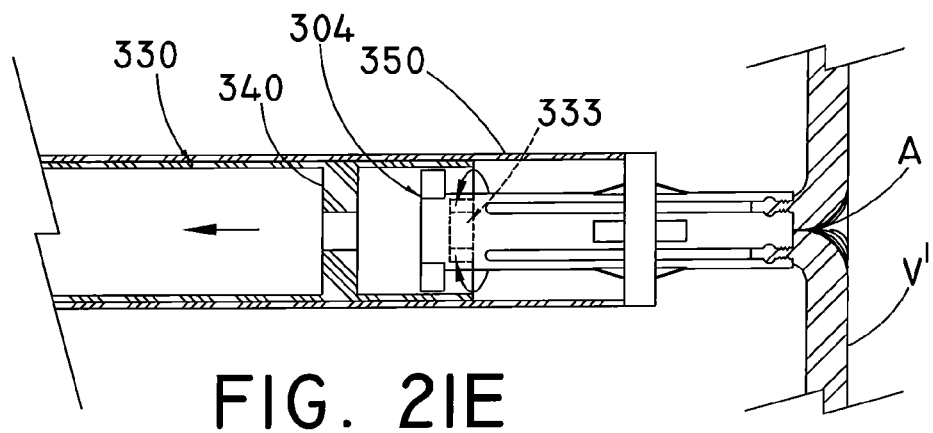

In FIG. 21C, the respective ribs and grooves in distal portion 333 of detachable arm 330, and in proximal body portion 304 of grasper 300, are sized and shaped such that proximal body portion 304 is receivable in the interior of the detachable arm. The respective ribs and grooves in the distal portion of detachable arm 330, and in the proximal body portion of grasper 300, are oriented relative to one another so that ribs 336 of detachable arm 330 inhibit the proximal body portion of grasper 300 from being removed. In FIG. 21D, grasper 300 can be positioned to be in place for closure of a vessel opening, which may urge proximal body portion 304 of grasper 300 to contact physical stop 340. Once the finger distal tips of grasper 300 engages the outer surface of the vessel wall, the tissue surrounding the vessel opening, a sheath 350 can be configured to engage and move closing member 320 to the second position, thereby locking the closing member in place and closing fingers 310, in similar manner as in FIG. 18. The physical stop 340 can contact the proximal end of the grasper to apply the pushing force necessary to maintain engagement with the outer vessel wall during the closing of the fingers. In FIG. 21E, detachable arm 330 can be removed from grasper 300. For example, detachable arm 330 can be repositioned, such as by rotation, so that the respective ribs and grooves in the distal portion of detachable arm 330, and in the proximal body portion of grasper 300, are in alignment relative to one another for removal by sliding the detachable arm away from the grasper. Sheath 350 can then be withdrawn in the proximal direction away from grasper 300, leaving the grasper in the body in a similar manner as shown in FIG. 20D. An introducer sheath (not shown) may be used to facilitate placement of the grasper, the detachable arm, and the sheath at the vessel opening.

Figure 21F:
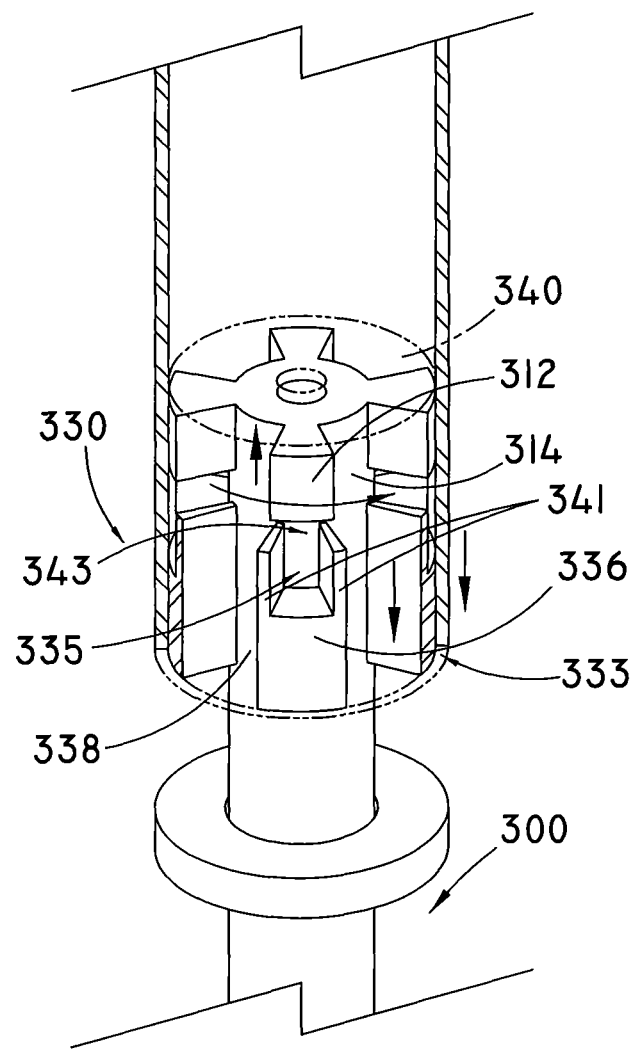

In FIG. 21F, in order to prevent premature disengagement of grasper 300 from detachable arm 330, a rotating inhibiting member 335 can be positioned within at least one groove 314 of the grasper 300. Rotating inhibiting member 335 can be one or more axial protrusions 341 extending proximally from rib 336. Protrusions 341 can be laterally spaced from one another to define a receiving chamber 343 that is sized to receive ribs 312 of grasper 300. When in delivery mode, each of ribs 312 can fit with chambers 343. When detachment is desired, detachable arm 330 can be pushed or moved distally relative to grasper 300, which can cause chambers 343 to be removed from a surrounding relationship with ribs 312. The protrusions are configured to extend partially toward physical stop 340 in order to allow sufficient clearance from the end of grasper 300 to move and rotate. A slight rotation of detachable arm 330 can move ribs 312 in alignment with grooves 338 so that the grasper can be detached. This functions in a similar manner as a push-down-and-turn coupling of a bottle. Rotating inhibiting member 335 may be an axial protrusion that extends from the distal surface of the physical stop partially toward distal end of the detachable arm 330 to allow spacing for moving and rotating the grasper. Rotating inhibiting member 335 may be a radial protrusion from the luminal wall of the detachable arm, instead of or in addition to the axial protrusion. Rotating inhibiting member 335 may be removable from groove 314 by the operator. In one example, rotating inhibiting member 335 can include a trigger wire or a rod that can extend through an aperture formed in the physical stop, and further extends through at least one groove 314 of grasper 300. The trigger wire can be released or the rod pulled by the operator from a proximal handle of the detachable arm as appreciated by one skilled in the art.

Figure 22A:
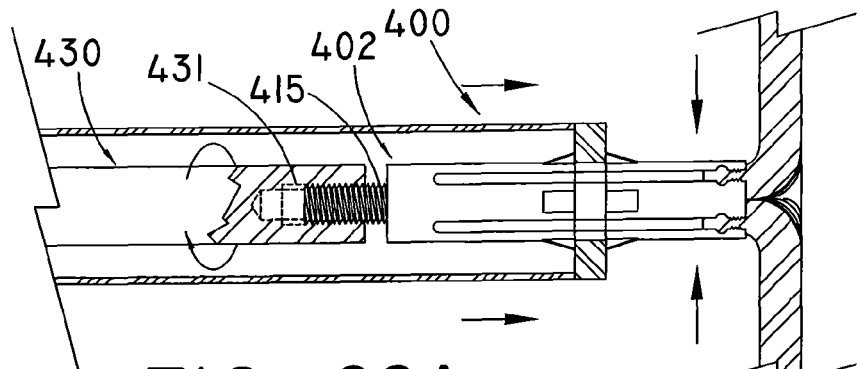
FIGS. 22A-B illustrate a further embodiment of a grasper.
Figure 22B:
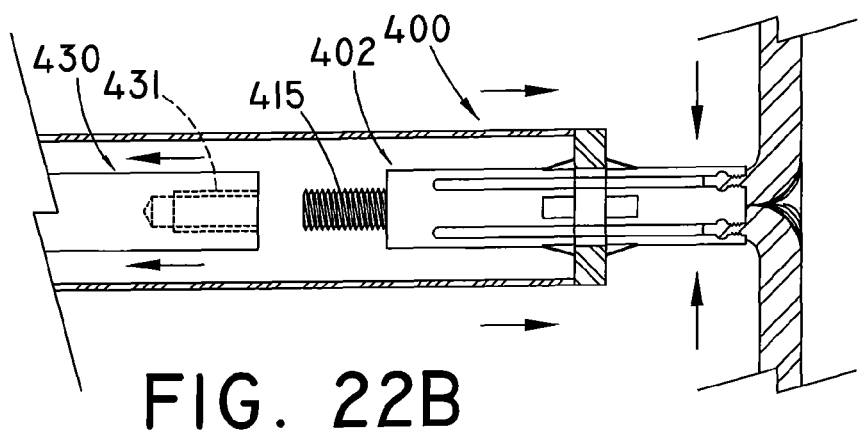
Figure 22C:
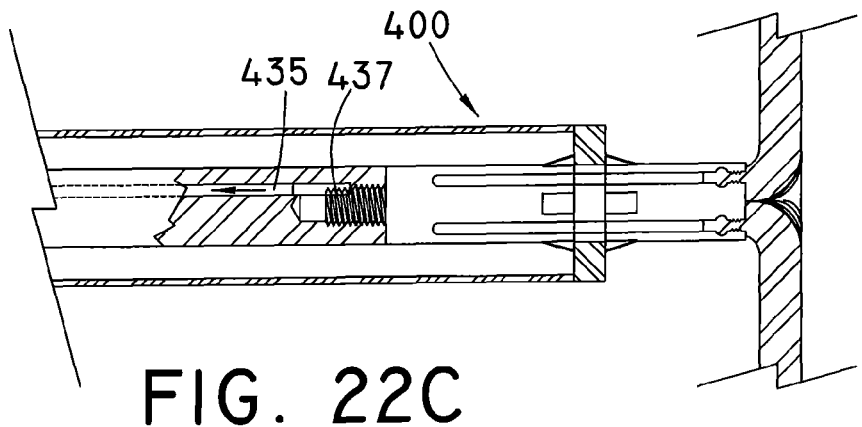

FIGS. 22A-B illustrate another embodiment of a bioabsorbable grasper 400. This embodiment is generally similar to that of FIGS. 21A-E, but instead of the rib and groove structure, the proximal end 402 of grasper 400 is provided with external screw threads 415. In the embodiment shown, detachable arm 430 is provided with internal screw threads 431 that are complementary with external screw threads 415. As appreciated by those skilled in the art, the detachable arm may be provided with the external screws of grasper 400, and the grasper may be provided with the internal screw threads of detachable arm. As shown, detachable arm 430 is threadably engaged with grasper 400, and can be removed from grasper 400 by relative rotational movement in an unlocking direction. Once disengaged, detachable arm 430 can be withdrawn away from grasper 400, leaving the grasper in the body in a similar manner as shown in FIG. 20D. In FIG. 22C, in order to prevent premature disengagement of grasper 400 from detachable arm 430, a rotating inhibiting member 435 can be positioned within at a notch 437 at the proximal end of grasper 400, so that the grasper is restricted from rotating to the position where it can be deployed. Rotating inhibiting member 435 can be removed from notch 437 by the operator so that the grasper can be rotated to the position for removal. In one example, the member can include a trigger wire or a rod that is positioned within an aperture of detachable arm 430.

Figure 23A:
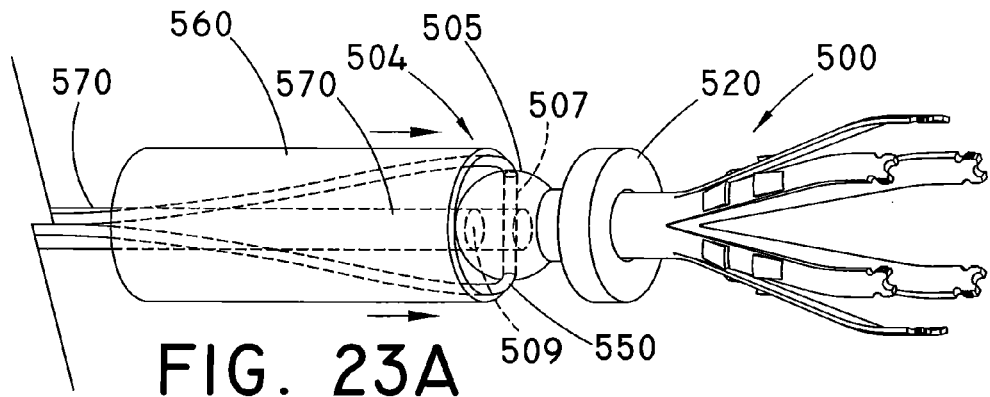
FIGS. 23A-B illustrate a still further embodiment of a grasper.
Figure 23B:
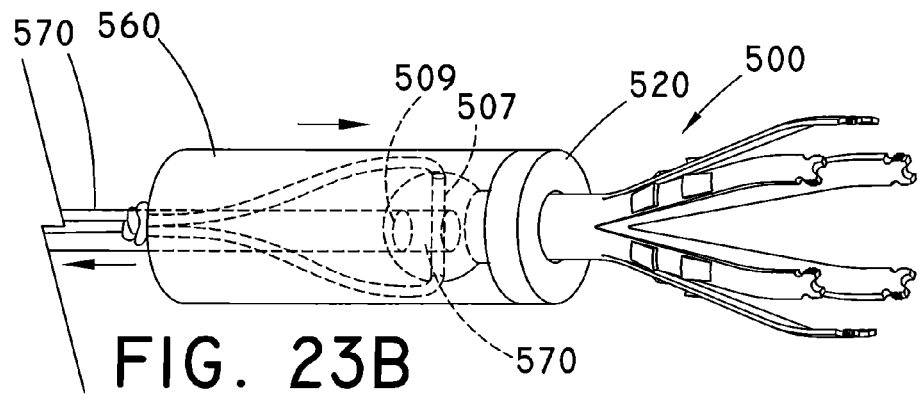

FIGS. 23A-B illustrate another embodiment of a bioabsorbable grasper 500. Grasper 500 is generally similar to grasper 200, and includes a proximal body portion 504 having a beaded end portion 505. Beaded end portion 505 includes an aperture 507 (shown in phantom) therethrough, which can extend generally perpendicular to the axis of the grasper. In this embodiment, the detachable arm comprises a flexible member, such as suture 550, that is threaded through aperture 507, and extends through an overlaying sheath 560. Sheath 560 is advanceable in the distal direction (as shown by the arrows in FIG. 23A), such that grasper 500 and the detachable arm are locked in place. The ends of the suture may be locked or otherwise retained in a fixed position such as being tied as shown, to lock tensionably into place. Sheath 560 can be moved relative to the detachable arm in order to move the closing member 520 into the locking position as shown in FIGS. 17 and 18. The detachable arm can be removed from grasper 500 by unlocking (e.g., untying or cutting) suture 550 in a manner to be removed from the aperture 507, leaving the grasper in the body in a similar manner as shown in FIG. 20D. As appreciated by those skilled in the art the grasper can be configured with a flexible member and the detachable arm can be configured with the aperture for receiving the flexible member, that is consistent with the description herein.

Figure 23C:
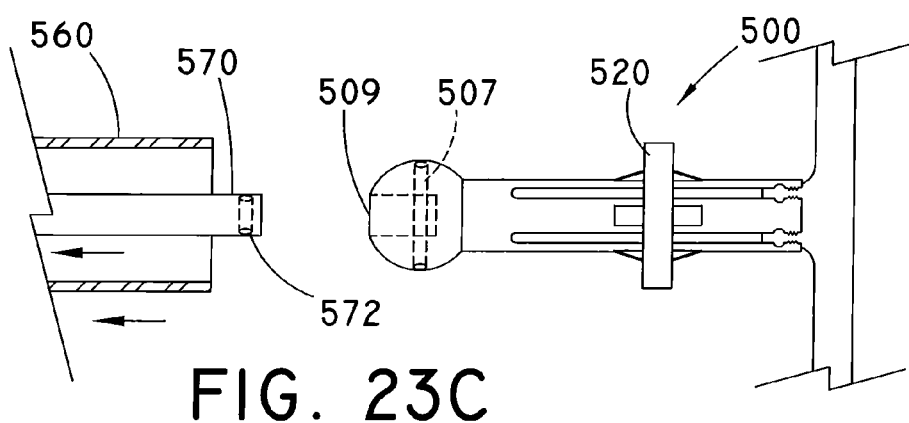

A pushrod 570 may also be included to facilitate an increase in pressure of grasper 500 against the body vessel. The pushrod 570 is shown extending through sheath 560 and through an aperture 509 formed in beaded end portion 505 of grasper 500, where aperture 509 is shown to extend generally parallel to the axis of the grasper. Aperture 509 may be in communication with aperture 507. Pushrod 570 also has a bore 572 extending therein for receiving suture 550 so that the suture coupled the pushrod to the grasper. In FIG. 23B, pushrod 570 can be pushed in the distal direction, as shown by the arrow, toward body vessel, while suture 550 is withdrawn in the proximal direction, as shown by the arrow, which can urge movement of the locking member 520 over the fingers for closure of grasper 500. As shown in FIG. 23, the discontinuity of suture 550 can release pushrod 570 and suture 550 from engagement with grasper 500.

Figure 25B:
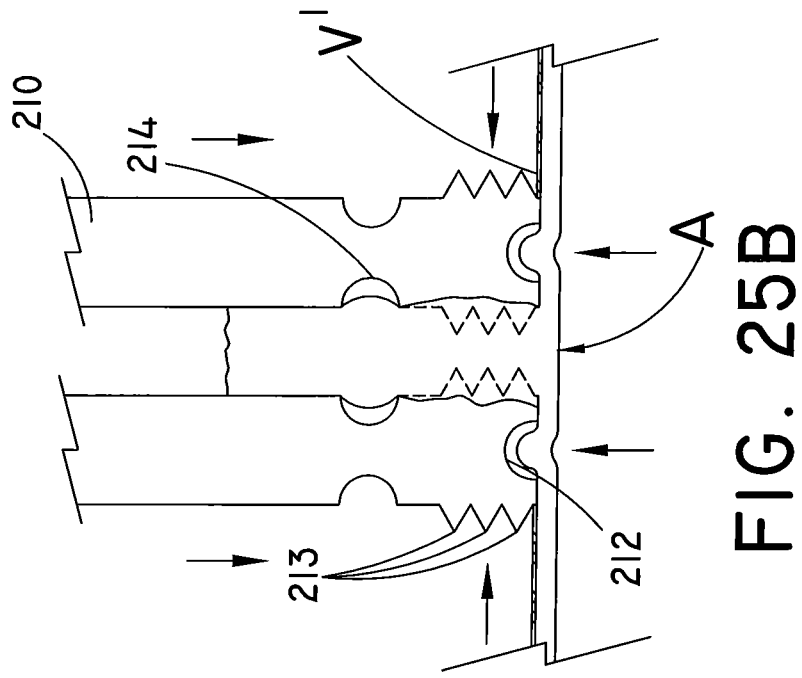
FIGS. 25A-B are enlarged partial views of a distal tip of the grasper of FIG. 16A.
Figure 25A:
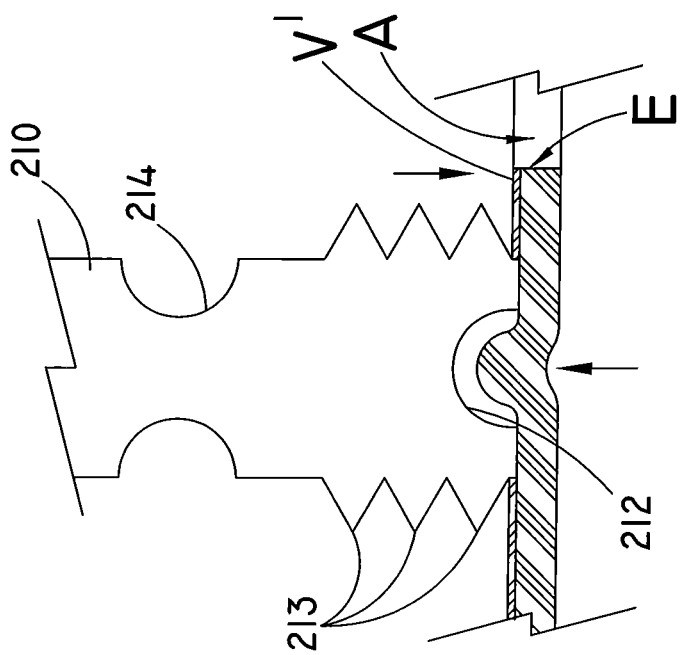

FIGS. 24A-24D, with corresponding top views in respective FIGS. 24E-24H, illustrate in more detail the grasping action of any of the embodiments of the grasper described herein (e.g., grasping member 22 or 202) of the outer vessel wall V1 and the closure of the vessel opening A in several stages. In FIGS. 24A and 24E, the distal tips of fingers 210 are shown in an open position initially engaging an outer wall portion of the vessel wall V1 surrounding opening A. It may be desirable to close the opening from external the vessel, instead of from internal the vessel. Devices that close from the internal the vessel typically have a component extending from within the vessel outward through the opening, typically allowing the opening to close only around the outward extending component which increase the potential for blood leakage, rather than closing in on itself. FIG. 25A illustrates in greater detail the distal tip of a finger 210 against a portion the outer vessel wall. Cut-out portion 212, as well as the blunt portions surrounding cut-out portion 212, can limit penetration of the distal tip of finger 210 into the tissue of the vessel wall during use, by allowing the tissue to fold into the cut-out portion 212 without piercing the tissue. The fingers are preferably without hooks or barbs that are intended and designed to pierce the vessel wall and possibly sever portions thereof, such as the vasa vasorum that supply blood and nutrients to the vessel wall. Hooks and barb can also be difficult to manipulate so that the tips are in position to actually penetrate the vessel wall, typically rocking or being unstable along the curved portion of the hook. In FIGS. 24B and 24F, the distal tips of fingers 210 are shown moving from the open position toward a closed position. Fingers 210 can move in a radial direction toward the center of the opening and can move in a lateral or circumferential direction closer to adjacent fingers. An edge E defining opening A is shown to initially move radially closer to itself and vertically within the fingers.

In FIGS. 24C and 24G, the distal tips of fingers 210 are shown moving closer to the closed position, where fingers 210 are closer to one another relatively in the radial and circumferential direction. Edge E is shown to move further radially closer to itself and move further vertically. In FIGS. 24D and 24H, the distal tips of fingers 210 are shown in the closed position, with closing member 220 in the locking position. Fingers 210 are brought in close proximity to one another in the radial and circumferential direction. Edge E is shown to move even further radially closer to itself and vertically so that edge E contacts itself, as well as the inner vessel wall portion adjacent the edge, to close vessel opening A. FIG. 25B illustrates in greater detail the distal tip of a pair of adjacent fingers 210 in the closed position against a portion the outer vessel wall. Teeth 213 along a lateral side of one finger cooperate with teeth 213 along a lateral side of an adjacent finger to facilitate grasping of the outer vessel wall. Cut-out portion 214 can provide a space into which the tissue may fold into.

Those skilled in the art will appreciate that other routine modifications may be made to the bioabsorbable vessel closure device as described herein for a particular purpose, which modifications are considered within the scope of the invention. Additional features of the construction or composition of the various elements of the vessel closure device not otherwise discussed herein are not believed to be critical to the present invention, so long as the recited elements possess the capability needed for them to perform as desired. Additional details of construction are believed to be well within the ability of one of ordinary skill in the art.

It is therefore intended that the foregoing detailed description be regarded as illustrative rather than limiting, and that it be understood that it is the following claims, including all equivalents, that are intended to define the spirit and scope of this invention.

The invention claimed is:

1. An implantable grasper for closure of an opening in a body vessel wall, comprising:
a grasping member comprising an integral tubular member having a proximal portion and a distal portion, said proximal portion comprising a generally tubular body and a proximal end, and said distal portion comprising a plurality of fingers extending radially from a distal end of said body at a first angle, and collapsible therefrom to a second angle, said fingers being defined by slits through said tubular member, wherein said fingers extend integrally from said tubular body, said fingers having a generally rectangular cross-section defined by a thickness and a width where said width is larger than said thickness, said width being defined by said slits and said thickness being defined by inner and outer surfaces of said tubular member, said fingers having a distal tip configured to non-piercingly grasp an outer wall portion of said body vessel surrounding said opening when said fingers are extended at said first angle, said distal tip including two generally flattened portions at a leading end thereof and a groove disposed between the generally flattened portions, said generally flattened portions each comprising a distally facing end surface defined by at least a portion of said rectangular cross-section; and
a locking member slidably received over a portion of said grasping member, the locking member movable along the fingers to collapse said fingers from said first angle to said second angle to cause said collapsed fingers to at least substantially close said vessel opening, said grasping member and said locking member being formed from a bioabsorbable composition.

2. The grasper of claim 1, where the proximal end of the proximal portion is at least one of a keyed structure or a keyway structure, having at least one alternating axial rib and axial groove.

3. The grasper of claim 1, where the proximal end of the proximal portion includes at least one of external threads along an outside surface or internal threads along a lumen extending through the proximal portion.

4. The grasper of claim 1, wherein the locking member comprises a proximal surface and a distal surface opposite the proximal surface, and wherein at least one of the fingers of the grasping member have one or more engaging members comprising a pair of protrusions formed on the outer surface of the finger, the engaging members being spaced apart to define a pre-determined locking position for the movable locking member therebetween, so that when in the locking position the locking member is inhibited from axial movement in either the proximal or distal directions by contact between one of the engaging members and at least one of the proximal surface and the distal surface.

5. The grasper of claim 4, wherein the one or more engaging members has a pair of confronting surfaces that are substantially perpendicular to an underlying surface.

6. The grasper of claim 4, wherein one of the protrusions has an inclined surface to facilitate distal movement of the locking member to an abutting relationship with a confronting surface of the other of the protrusions.

7. The grasper of claim 6, wherein the one or more engaging members further defines one or more walls of a recess.

8. The grasper of claim 4, wherein at least one of said fingers of the grasping member and the locking member are structured and arranged to provide tactile feedback in response to the locking member being positioned in a predetermined locking position.

9. The device of claim 1, wherein said distal tip of said fingers includes a cut-out portion along a lateral side of said finger for non-piercingly grasping and/or securing tissue around said opening, said lateral side extending between said inner and outer surfaces and defining at least one side of said width.

10. The device of claim 1, wherein said distal tip of said fingers includes a plurality of teeth along a lateral side of said finger for non-piercingly grasping and/or securing tissue around said opening, said lateral side extending between said inner and outer surfaces and defining at least one side of said width.

11. The device of claim 10, wherein said distal tip of said fingers includes a cut-out portion along said lateral side of said finger proximal from said teeth for non-piercingly grasping and/or securing tissue around said opening.

12. The device of claim 11, wherein said grasping member consists of six of said fingers.

13. The device of claim 1, wherein said grasping member consists of six of said fingers.

14. The device of claim 1, wherein an outer diameter of said grasping member is within 0.75 and 2 mm.

15. The device of claim 1, wherein the locking member has a distal surface and where at least one of said fingers of the plurality of said fingers of the grasping member has a protrusion formed on its outer surface, the protrusion contacting the distal surface of the locking member to inhibit the locking member from axial movement in a distal direction after the fingers are collapsed.

16. A system for closure of an opening in a body vessel wall of a body, comprising:
a bioabsorbable grasping member comprising an integral tubular member having a proximal end, a proximal generally tubular body, and a plurality of collapsible fingers extending radially from a distal end of said proximal generally tubular body, said fingers being defined by slits through said tubular member, wherein said fingers extend integrally from said tubular body, said fingers having a generally rectangular cross-section defined by a thickness and a width where said width is larger than said thickness, said width being defined by said slits and said thickness being defined by inner and outer surfaces of said tubular member, said fingers having a distal tip, the distal tip comprising at least one of: one or more first cut-out portions at an axial end of said distal tip, one or more teeth along at least one of a pair of lateral sides of said fingers, and a second cut-out portion along at least one of said lateral sides proximal of said teeth, said distal tip configured to non-piercingly grasp an outer wall portion of said body vessel surrounding said opening when said fingers are extended in an open position, said distal tip including two generally flattened portions at a leading end thereof and a groove disposed between the generally flattened portions, said generally flattened portions each comprising a distally facing end surface defined by at least a portion of said rectangular cross-section;
a bioabsorbable locking member slidably coupled over a portion of the grasping member, where the locking member is movable to collapse said fingers from the open position to a closed position to cause said collapsed fingers to at least substantially close said vessel opening; and
a detachable arm removably attached to the grasping member so that the grasping member and the locking member can remain in the body after detachment of the detachable arm from the grasping member.

17. The system of claim 16, where a distal portion of the detachable arm frictionally contacts a portion of the grasping member, where said detachable arm detaches from said grasping member without manipulation of the detachable arm.

18. The system of claim 16, where the detachable arm includes a proximal portion and a distal portion, said distal portion comprising a plurality of collapsible fingers extending radially from a distal end of said proximal portion of the detachable arm in an open position,
the system further comprising a sheath slidably received over a portion of the detachable arm, the sheath configured to collapse said fingers of the detachable arm from said open position to a closed position to cause a portion of said collapsed fingers to frictionally contact a portion of the grasping member, where withdrawal of the sheath permits said fingers to radially extend to the open position so that said fingers are removed from contact with said portion of the grasping member.

19. The system of claim 16, where one of the detachable arm and the grasping member has a keyed structure, having at least one alternating rib and groove, and the other of the detachable arm and the grasping member has a keyway structure, having at least one alternating rib and groove structured and arranged to cooperatively interface with the at least one alternating rib and groove of the keyed structure, where alignment of the groove of one and the rib of the other permits detachment of the grasping member from the detachable arm.

20. The system of claim 16, where one of the detachable arm and the grasping member has external threads, and the other of the detachable arm and the grasping member has internal threads configured to threadably engage with the external threads, where rotational movement of the detachable arm relative to the grasping member in a loosening direction permits detachment of the grasping member from the detachable arm.

21. The system of claim 16, where one of the detachable arm and the grasping member has a flexible member, and the other of the detachable arm and the grasping member has an aperture configured to receive the flexible member, where removal of the flexible member from said aperture permits detachment of the grasping member from the detachable arm.

22. The system of claim 16, further comprising an anchor member having a distal end portion, said distal end portion having a non-expanded condition and an expanded condition, said anchor member configured such that said distal end portion is passable through a passageway of said body of said grasping member in said non-expanded condition, and expandable to said expanded condition upon passage therethrough.

23. The system of claim 16, further comprising a locking sheath having a lumen extending therein, where the detachable arm is slidably received in the lumen of the locking sheath, the locking sheath having a distal end configured to move the locking member to a position surrounding the fingers.

24. The system of claim 23, further comprising an introducer sheath having a lumen extending therein, where the lumen of the introducer sheath is configured to contain the locking sheath, the detachable arm, the grasping member, and the locking member for delivery to the opening of the body vessel wall, where withdrawal of the introducer sheath therefrom permits radial extension of the fingers of the grasping member to the open position.

25. A method for closing an opening at an access site in a body vessel, comprising:

providing a closure device for said opening, said closure device comprising: a grasping member comprising an integral tubular member having a proximal portion and a distal portion, said proximal portion comprising a generally tubular body and said distal portion comprising a plurality of grasping fingers extending from a distal end of said proximal portion, said fingers radially extending from said proximal portion distal end in an open position, and radially collapsible therefrom to a closed position, said fingers being defined by slits through said tubular member, wherein said fingers extend integrally from said tubular body, said fingers having a generally rectangular cross-section defined by a thickness and a width where said width is larger than said thickness, said width being defined by said slits and said thickness being defined by inner and outer surfaces of said tubular member, said fingers having a distal tip configured to non-piercingly grasp tissue of said body vessel surrounding said opening when said fingers are extended in the open position, said distal tip including two generally flattened portions at a leading end thereof and a groove disposed between the generally flattened portions, said generally flattened portions each comprising a distally facing end surface defined by at least a portion of said rectangular cross-section, a closing member slidable relative to a portion of said grasping member for radially collapsing said fingers from said open position to said closed position, each of said grasping member and said closing member being formed from a bioabsorbable composition;

a stabilizing member engageable with said proximal portion of the grasping member; and a locking sheath slidable over said stabilizing member and at least a portion of said grasping member;

arranging said grasping member to said open position such that the distal tip of said fingers engage tissue surrounding said opening; and advancing said locking sheath over said stabilizing member and a length of said grasping member, such that said locking sheath engages and advances said closing member over a length of said fingers, thereby collapsing said fingers to the closed position to at least substantially close said vessel opening at the access site in the body vessel.

* * * * *